United States Patent
Yanagihara et al.

(10) Patent No.: US 6,787,502 B2
(45) Date of Patent: Sep. 7, 2004

(54) GUANIDINE COMPOUND AND HEAT SENSITIVE RECORDING MATERIAL

(75) Inventors: Naoto Yanagihara, Shizuoka-ken (JP); Hisao Yamada, Shizuoka-ken (JP); Mitsuyuki Tsurumi, Shizuoka-ken (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 50 days.

(21) Appl. No.: 09/907,566

(22) Filed: Jul. 19, 2001

(65) Prior Publication Data

US 2002/0065194 A1 May 30, 2002

Related U.S. Application Data

(62) Division of application No. 09/477,545, filed on Jan. 4, 2000, now Pat. No. 6,348,529.

(30) Foreign Application Priority Data

Feb. 26, 1999 (JP) .............................. 11-050594

(51) Int. Cl.⁷ ............................................... B41M 5/30
(52) U.S. Cl. ...................... 503/208; 503/209; 503/216; 503/217
(58) Field of Search ............................. 503/208, 209, 503/216, 217

(56) References Cited

U.S. PATENT DOCUMENTS 4,828,957 A * 5/1989 Yonese et al. .............. 430/138

FOREIGN PATENT DOCUMENTS

| JP | 60-61288 | 4/1985 |
| JP | 61-104887 | 5/1986 |
| JP | 62-85987 | 4/1987 |
| JP | 2-223476 | 9/1990 |
| JP | 4-147135 | 5/1992 |
| JP | 4-197783 | 7/1992 |
| JP | 4-201483 | 7/1992 |

* cited by examiner

Primary Examiner—B. Hamilton Hess
(74) Attorney, Agent, or Firm—Sughrue Mion, PLLC

(57) ABSTRACT

An object of the present invention is to provide a heat sensitive recording material which can develop color at high density by the inclusion of a novel guanidine compound which is strongly basic and superior in diffusion resistance. The present invention for attaining the above-described object is a heat sensitive recording material comprising a substrate supporting thereon a heat sensitive recording layer containing a diazonium salt compound, a coupler which reacts with the diazonium salt compound when heated to develop color, and a base, wherein the heat sensitive recording layer includes as the base at least one of the guanidine compounds represented by the general formula (1):

General formula (I)

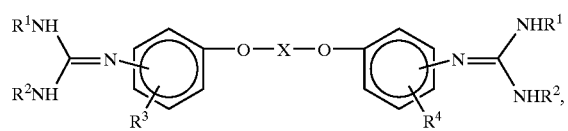

wherein, in the general formula (1), $R^1$ and $R^2$ represent an alkyl group or aryl group and may be the same or different, $R^3$ and $R^4$ represent a hydrogen atom, alkyl group or halogen atom and may be the same or different, and X represents a divalent connecting group.

5 Claims, No Drawings

GUANIDINE COMPOUND AND HEAT SENSITIVE RECORDING MATERIAL

This application is a Divisional of Ser. No. 09/477,545 filed Jan. 4, 2000, now U.S. Pat. No. 6,348,529.

BACKGROUND OF THE INVENTION

1. Field of the Invention

The present invention relates to a guanidine compound and a heat sensitive recording material and particularly, to a novel guanidine compound, and a novel heat sensitive recording material which can develop color at high image density by the inclusion of a diazonium salt compound and a coupler as color developing components and of the above-described guanidine compound as a base.

2. Description of the Related Art

Diazonium salt compounds form an azo dye by reacting with a compound called a coupler such as a phenolic derivative and the like, and at the same time, have photosensitivity and are decomposed by irradiation with light to lose the activity thereof. Therefore, diazonium salt compounds have been used for a long time as light recording materials typified by diazo copy (cf. "Basics of Photographic Technology (shashin kogaku no kiso)—the chapter on non-silver salt photography (higinen shashin hen)—" published by Japan Photographic Society (nippon shashin gakkai), corona corp., (1982) pp 89 to 117 and 182 to 201).

Further, diazonium salt compounds have recently been used for recording materials for which require fixation of an image by utilizing the fact that they are decomposed by light to lose their activity. Typical examples include light fixation type heat sensitive recording materials in which a diazonium salt compound and a coupler are heated according to image signals and allowed to react to form an image which is then fixed by irradiation with light (Koji Sato et al., Image Electron Society Bulletin (gazo denshi gakkai shi), vol. 11, No 4 (1982), pp 290 to 296, and the like).

In these heat sensitive recording materials, it is necessary for the diazonium salt and coupler to react immediately to develop color when heated, and conventionally organic salts such as tertiary amines, piperidines, piperazines, amidines, formamidines, pyridines, guanidines, morpholines and the like are added for the purpose of promoting the coupling reaction of the diazonium salt compound with the coupler. Among these, triphenylguanidine whose conjugated acid has a pKa of 7 has been mainly used for the guanidines.

However, when the reactivity of a diazonium salt compound with a coupler is low, a stronger base is required.

On the other hand, a multicolor heat sensitive recording material can be obtained by laminating heat sensitive recording layers developing different hues. The layer structure is not particularly restricted, and one example is a multicolor heat sensitive recording material in which a double heat sensitive recording layer comprising a combination of two kinds of diazonium salt compounds having different photosensitive wavelengths and couplers which develop different hues by reacting when heated with the respective diazonium salt compounds is laminated with a heat sensitive recording layer comprising a combination of an electron donative colorless dye with an electron receptive compound.

When a strong base as described above is used in the diazo heat sensitive recording layer of this type of multicolor heat sensitive recording material, it is necessary for the strong base to be superior in diffusion resistance so as not to influence other layers.

In view of the above circumstances, an object of the present invention is to provide a novel guanidine compound which is strongly basic and superior in diffusion resistance, and a novel diazo heat sensitive recording material which can develop color at high image density by the inclusion of a diazonium salt compound and a coupler as color developing components and of the guanidine compound as a base.

SUMMARY OF THE INVENTION

After intensive research into the structure of a guanidine compound in order to attain the above-described objective, the present inventors discovered the following facts (1) and (2), thus completing the present invention.

(1): Basicity increases by the substitution of an alkyl group for at least one of the three phenyl groups in triphenylguanidine owing to the substituent effect of the alkyl group.

(2): By forming bis type structure, the diffusion of a base into other layers can be prevented, and when a multi-layer structure is adopted, the color developing density in the layer which includes the base does not decrease and a deleterious influence is not exerted on other layers.

Namely, the first guanidine compound of the present invention is represented by the following general formula (1):

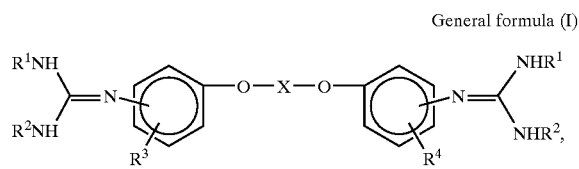

General formula (I)

(in general formula (1), $R^1$ and $R^2$ represent an alkyl group or aryl group. $R^1$ and $R^2$ may be the same or different. $R^3$ and $R^4$ represent a hydrogen atom, alkyl group or halogen atom. $R^3$ and $R^4$ may be the same or different. X represents a divalent connecting group.).

The second guanidine compound of the present invention is represented by the following general formula (2):

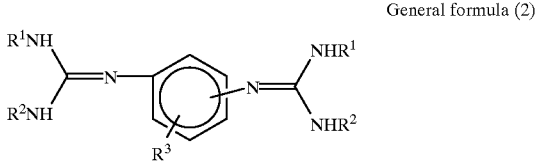

General formula (2)

(in general formula (2), $R^1$ and $R^2$ represent an alkyl group or aryl group. $R^1$ and $R^2$ may be the same or different. $R^3$ represents a hydrogen atom, alkyl group or halogen atom.).

The third guanidine compound of the present invention is represented by the following general formula (3):

General formula (3)

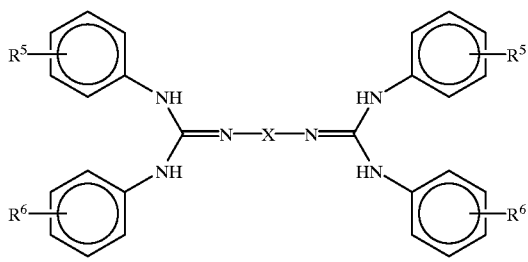

General formula (5)

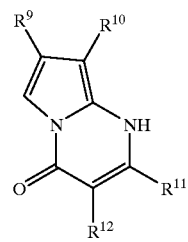

(in general formula (3), $R^5$ and $R^6$ represent a hydrogen atom, alkyl group or halogen atom. $R^5$ and $R^6$ may be the same or different. X represents an alkylene group.).

The first heat sensitive recording material of the present invention is a material comprising a substrate supporting thereon a heat sensitive recording layer comprising a diazonium salt compound, a coupler which reacts with the diazonium salt compound and develops color when heated, and a base, wherein the heat sensitive recording layer includes as the base at least one guanidine compound represented by general formula (1) according to the above-described first invention.

The second heat sensitive recording material of the present invention is a material comprising a substrate supporting thereon a heat sensitive recording layer comprising a diazonium salt compound, a coupler which reacts with the diazonium salt compound and develops color when heated, and a base, wherein the heat sensitive recording layer includes as the base at least one guanidine compound represented by general formula (2) according to the above-described second invention.

The third heat sensitive recording material of the present invention is a material comprising a substrate supporting thereon a heat sensitive recording layer comprising a diazonium salt compound, a coupler which reacts with the diazonium salt compound and develops color when heated, and a base, wherein the heat sensitive recording layer includes as the base at least one guanidine compound represented by general formula (3) according to the above-described third invention.

The fourth heat sensitive recording material of the present invention is a material comprising a substrate supporting thereon a heat sensitive recording layer comprising a diazonium salt compound, a coupler which reacts with the diazonium salt compound and develops color when heated, and a base, wherein the heat sensitive recording layer includes as the base at least one guanidine compound represented by general formula (4):

General formula (4)

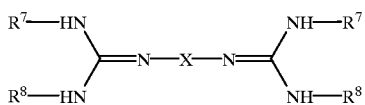

(in general formula (4), $R^7$ and $R^8$ represent an alkyl group. $R^7$ and $R^8$ may be the same or different. X represents a divalent connecting group.).

It is preferable that a heat sensitive recording material of the present invention comprises as the above-described coupler at least one pyrrolo [1,2-a] pyrimidine compound represented by the following general formula (5):

(in general formula (5), $R^9$ to $R^{12}$ represents a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group.).

In a heat sensitive recording material of the present invention, it is preferable to use a diazonium salt compound having a maximum absorption wavelength λmax of 450 nm or less in view of the hue and light fixation properties thereof, and it is more preferable to use at least one diazonium salt compound selected from compounds represented by the following general formula (6), compounds represented by the following general formula (7) and compounds represented by the following general formula (8):

General formula (6)

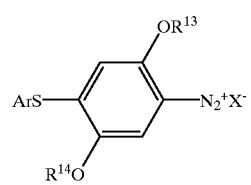

(in general formula (6), Ar represents a substituted or unsubstituted aryl group. Each of $R^{13}$ to $R^{14}$ represents a substituted or unsubstituted alkyl group, or a substituted or unsubstituted aryl group. $R^{13}$ to $R^{14}$ maybe the same or different. $X^-$ represents an acid anion.), General formula (7)

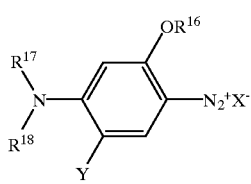

(in general formula (7), each of $R^{16}$, $R^{17}$ and $R^{18}$ represents a substituted or unsubstituted alkyl group, or a substituted or unsubstituted aryl group. $R^{16}$, $R^{17}$ and $R^{18}$ may be the same or different. Y represents a hydrogen atom or $-OR^{15}$ group. $R^{15}$ represents a substituted or unsubstituted alkyl group, or a substituted or unsubstituted aryl group. $X^-$ represents an acid anion.), General formula (8)

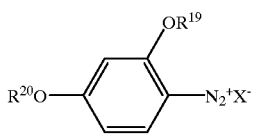

(in general formula (8), each of $R^{19}$ and $R^{20}$ represents a substituted or unsubstituted alkyl group, or a substituted or unsubstituted aryl group. $X^-$ represents an acid anion.)

DESCRIPTION OF THE PREFERRED EMBODIMENTS

The present invention will be described in detail below.

In the present invention, the following four kinds of guanidine compounds (hereinafter, may be referred to as "guanidine bases") are used as bases.

The first guanidine compound of the present invention has the structure represented by the above-described general formula (1).

In general formula (1), $R^1$ and $R^2$ represent an alkyl group or aryl group. $R^1$ and $R^2$ may be the same or different.

The alkyl group represented by $R^1$ and $R^2$ may be straight or branched, or may have an unsaturated bond. Further, these alkyl groups may be substituted by an alkoxy group, halogen atom, aryl group and the like.

As the alkyl group represented by $R^1$ and $R^2$, an alkyl group having 1 to 10 carbon atoms is preferable, and examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, 2-methoxyethyl group, 2-chloroethyl group, benzyl group, 2-phenylethyl group and the like.

The aryl group represented by $R^1$ and $R^2$ may be substituted by an alkyl group having 1 to 4 carbon atoms, an alkoxy group having 1 to 4 carbon atoms, or a halogen atom such as a chlorine atom and the like.

As the aryl group represented by $R^1$ and $R^2$, an aryl group having 6 to 10 carbon atoms is preferable, and examples thereof include a phenyl group, methylphenyl group, chlorophenyl group, methoxyphenyl group, ethoxyphenyl group, propoxyphenyl group, isopropoxyphenyl group, butoxyphenyl group and the like.

In the above-described general formula (1), $R^3$ and $R^4$ represent a hydrogen atom, alkyl group or halogen atom.

The alkyl group represented by $R^3$ and $R^4$ may be straight or branched, and may have an unsaturated bond.

As the alkyl group represented by $R^3$ and $R^4$, an alkyl group having 1 to 4 carbon atoms is preferable, and examples thereof include a methyl group, trifluoromethyl group, ethyl group, butyl group, propyl group, isopropyl group, isobutyl group, sec-butyl group, t-butyl group and the like.

As the halogen atom represented by $R^3$ and $R^4$, a fluorine atom, chlorine atom, bromine atom and the like are listed, and a chlorine atom is preferable from among these.

$R^3$ and $R^4$ may be the same or different.

In the above-described general formula (1), X represents a divalent connecting group.

As the divalent connecting group represented by X, an alkylene group having 1 to 20 carbon atoms, a phenylene group having 6 to 20 carbon atoms, and a xylene group having 8 to 20 carbon atoms are preferable, and this alkylene group may be straight or branched, and may have an oxygen atom or nitrogen atom in its chain. Examples thereof include a methylene group, trimethylene group, propylene group, tetramethylene group, hexamethylene group, decamethylene group, p-xylylene group, m-xylylene group, —CH$_2$CH$_2$OCH$_2$CH$_2$—, —CH$_2$CH$_2$N(CH$_3$)CH$_2$CH$_2$— and the like.

The second guanidine compound of the present invention has the structure represented by the above-described general formula (2).

In general formula (2), $R^1$ and $R^2$ have the same definitions as for $R^1$ and $R^2$ in general formula (1), and represent the same alkyl group or aryl group. $R^1$ and $R^2$ may be the same or different.

$R^3$ has the same definition as for $R^3$ in general formula (1), and represents the same hydrogen atom, alkyl group or halogen atom.

The third guanidine compound of the present invention has structure represented by the above-described general formula (3).

In general formula (3), $R^5$ and $R^6$ have the same definitions as for $R^3$ and $R^4$ in general formula (1), and represent the same hydrogen atom, alkyl group or halogen atom. $R^5$ and $R^6$ may be the same or different.

In general formula (3), X represents an alkylene group. As this alkylene group, an alkylene group having 1 to 20 carbon atoms is preferable, and it may be straight or branched, or may have an oxygen atom or nitrogen atom in its chain.

The fourth guanidine compound of the present invention has the structure represented by the above-described general formula (4).

In general formula (4), $R^7$ and $R^8$ represent and alkyl group. $R^7$ and $R^8$ may be the same or different.

The alkyl group represented by $R^7$ and $R^8$ may be straight or different, or may have an unsaturated bond. Further, these alkyl groups may be substituted by an alkoxy group having 1 to 4 carbon atoms, or a halogen atom.

As the alkyl group represented by $R^7$ and $R^8$, an alkyl group having 1 to 10 carbon atoms is preferable, and examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, 2-methoxyethyl group, 2-chloroethyl group and the like.

In the above-described general formula (4), X is identical to the X described in the above-described general formula (1), and represents the same divalent connecting group.

Typical specific examples of a guanidine compound of the present invention suitably used as a base include, but are not limited to, the following compounds.

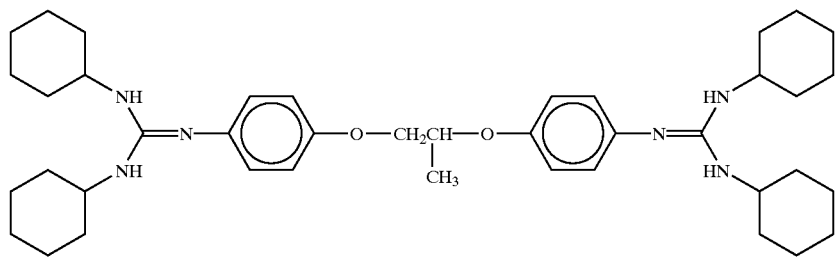
(1)-1
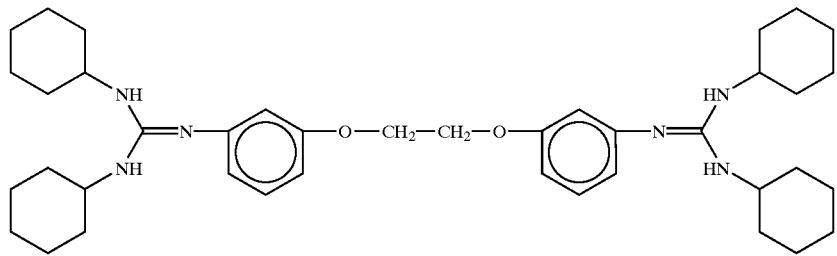
(1)-2
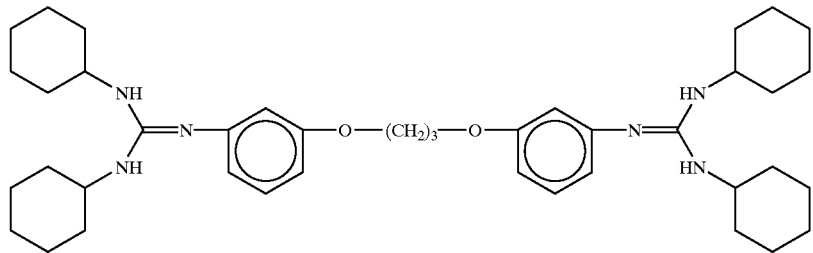
(1)-3
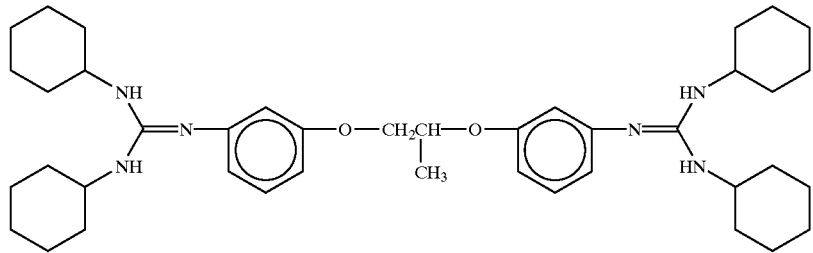
(1)-4
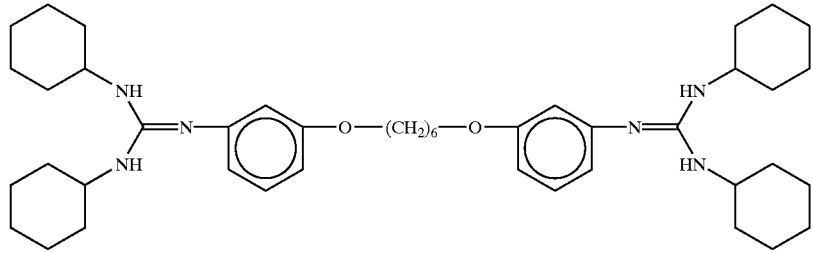
(1)-5
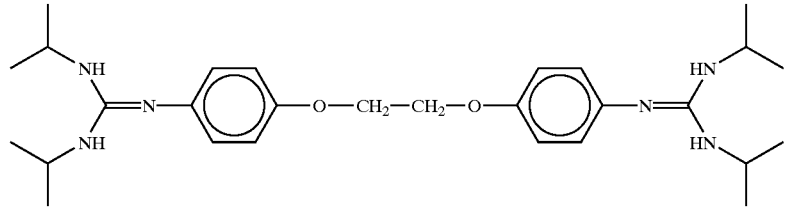
(1)-6

-continued
(1)-7
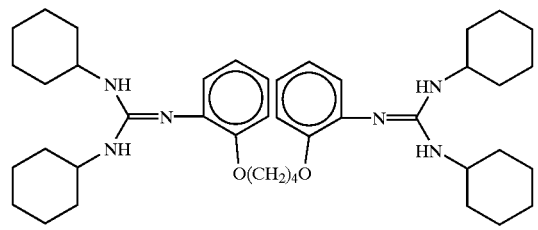
(2)-1
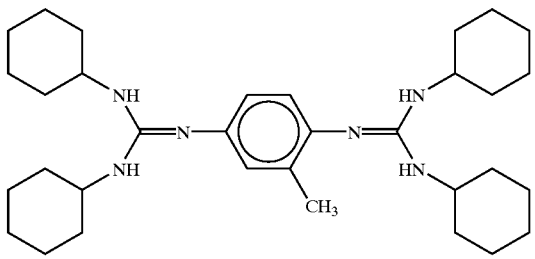
(2)-2
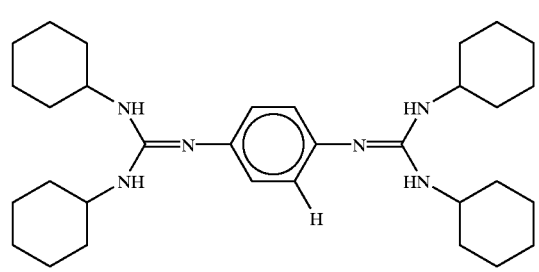
(2)-3
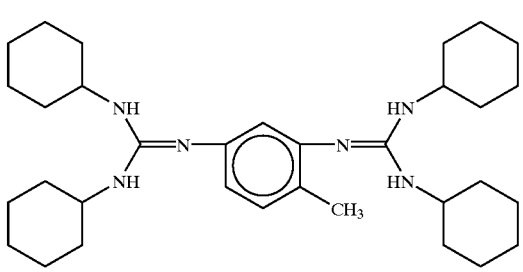
(2)-4
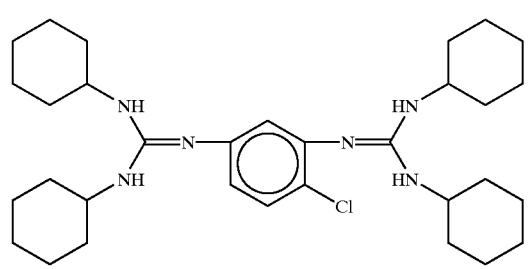
(2)-5
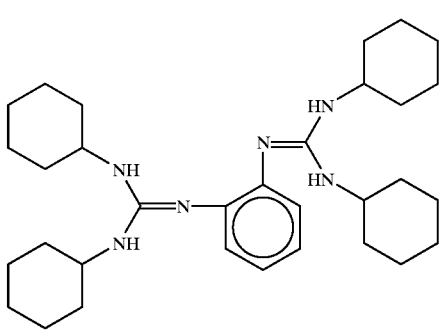
(2)-6
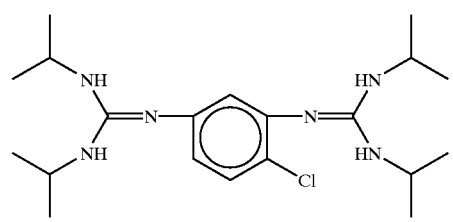
(3)-1
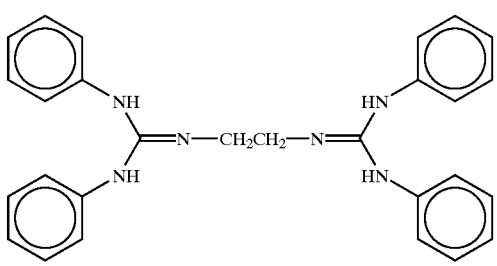
(3)-2
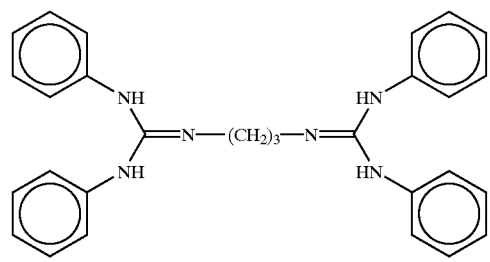
(3)-3
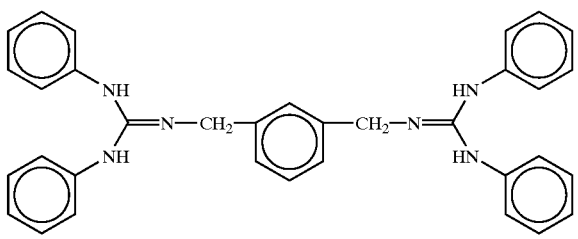

-continued

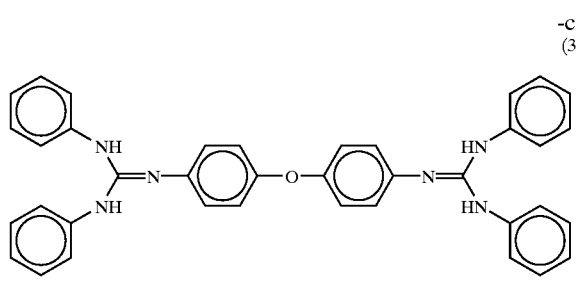
(3)-4

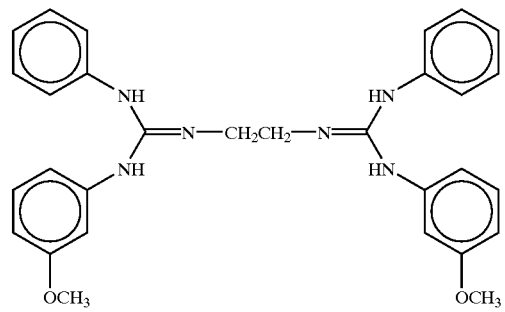
(3)-5

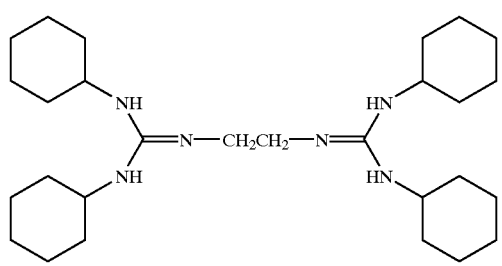
(4)-1

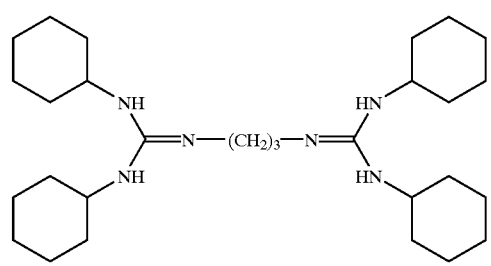
(4)-2

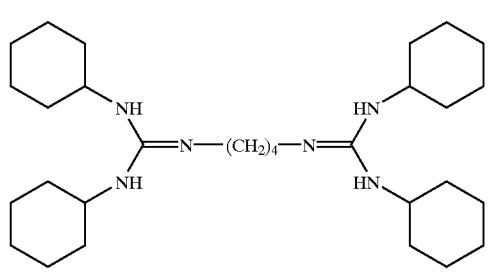
(4)-3

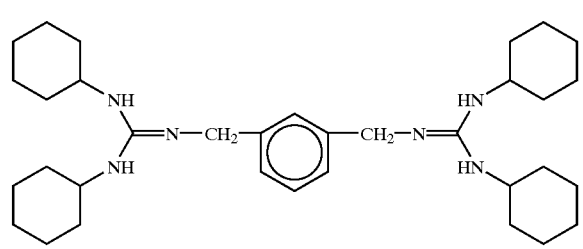
(4)-4

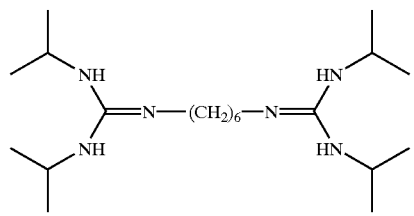
(4)-5

Guanidine compounds represented by any of the general formulae (1) to (4) may be used alone or in combination of two of more.

The guanidine compound of the present invention can be used together with another known base depending on the objective.

Examples of the other base include organic bases such as tertiary amines, piperidines, piperazines, amidines, formamidines, pyridines, guanidines, morpholines and the like, and these are used in an amount which does not decrease the effect of the base in the present invention.

Specific examples of the above-described organic base include piperazines such as N,N'-bis(3-phenoxy-2-hydroxypropyl)piperazine, N,N'-bis [3-(p-methylphenoxy)-2-hydroxypropyl]piperazine, N,N'-bis [3-(p-methoxyphenoxy)-2-hydroxypropyl]piperazine, N,N'-bis(3-phenylthio-2-hydroxypropyl)piperazine, N,N'-bis [3-(β-naphthoxy)-2-hydroxypropyl]piperazine, N-3-(β-naphthoxy)-2-hydroxypropyl-N'-methylpiperazine, 1,4-bis {[3-(N-methylpiperazino)-2-hydroxy]propyloxy} benzene and the like, morpholines such as N-[(3-(β-naphthoxy)-2-hydroxy]propylmorpholine, 1,4-bis[3-morpholino-2-hydroxy)propyloxy]benzene, 1,3-bis[(3-morpholino-2-hydroxy)propyloxy]benzene and the like, piperidines such as N-(3-phenoxy-2-hydroxypropyl)piperidine, N-dodecylpiperidine and the like, triphenylguanidine, tricyclohexylguanidine, dicyclohexylphenylguanidine, 2-N-methyl-N-benzylaminoethyl 4-hydroxybenzoate, 2-N,N-di-n-butylaminoethyl 4-hydroxybenzoate, 4-(3-N,N-dibutylaminopropoxy)benzenesulfoneamide, 4-(2-N,N-dibutylaminoethoxycarbonyl)phenoxyacetic amide and the like.

The details of these are described in Japanese Patent Application Laid-Open (JP-A) Nos. 57-123086, 60-49991, 60-94381, Japanese Patent Application Nos. 7-228731, 7-235157, 7-235158 and the like. These organic groups may be used alone or in combination of two or more.

The amount of the base used in the present invention is not particularly restricted, and is preferably from 1 to 30 mol, and more preferably from 1 to 5 mol based on 1 mol of the above-described diazonium salt compound.

The coupler which can be used in the present invention is not particularly restricted providing it couples with a diazo compound to form a dye in a basic atmosphere and/or a neutral atmosphere, and known couplers can be used depending on various objectives such as hue adjustment and the like. As such couplers, so-called active methylene compounds having a methylene group adjacent to a carbonyl group, phenol derivatives, naphthol derivatives and the like are listed, and the following compound are listed as specific examples thereof.

Examples of the above-described coupler include resorcin, fluoroglucine, 2,3-dihydroxynaphthalene, sodium 2,3-dihydroxynaphthalene-6-sulfonate, 1-hydroxy-2-naphtoic morpholinopropylamide, sodium 2-hydroxy-3-naphthalenesulfonate, 2-hydroxy-3-naphthalenesulfonic anilide, 2-hydroxy-3-naphthalenesulfonic morpholinopropylamide, 2-hydroxy-3-naphthalenesulfonic 2-ethylhexyloxypropylamide, 2-hydroxy-3-naphthalenesulfonic 2-ethylhexylamide, 5-acetamide-1-naphthol, sodium 1-hydroxy-8-acetamidenaphthalene-3,6-disulfonate, 1-hydroxy-8-acetamidenaphthalene-3,6-disulfonic dianilide, 1,5-dihydroxynaphthalene, 2-hydroxy-3-naphthoic morpholinoproylamide, 2-hydroxy-3-naphthoic octylamide, 2-hydroxy-3-naphtoic anilide, 5,5-dimethyl-1,3-cyclohexanedione, 1,3-cyclopentanedione, 5-(2-n-tetradecyloxyphenyl)-1,3-cyclohexanedione, 5-phenyl-4-methoxycarbonyl-1,3-cyclohexanedione, 5-(2,5-di-n-octyloxyphenyl)-1,3-cyclohexanedione, N,N'-dicyclohexylbarbituric acid, N,N'-di-n-dodecylbarbituric acid, N-n-octyl-N'-n-octadecylbarbituric acid, N-phenyl-N'-(2,5-di-n-octyloxyphenyl)barbituric acid, N,N'-bis (octadecyloxycarbonylmethyl)barbituric acid, 1-phenyl-3-methyl-5-pyrazolone, 1-(2,4,6-trichlorophenyl)-3-anilino-5-pyrazolone, 1-(2,4,6-trichlorophenyl)-3-benzamide-5-pyrazolone, 6-hydroxy-4-methyl-3-cyano-1-(2-ethylhexyl)-2-pyridone, 2,4-bis-(benzoylacetamide)toluene, 1,3-bis-(pivaloylacetamidemethyl)benzene, benzoylacetonitrile, thenoylacetonitrile, acetacetanilide, benzoylacetanilide, pivaloylacetanilide, 2-chloro-5-(N-n-butylsulfamoyl)-1-pivaloylacetamidebenzene, 1-(2-ethylhexyloxypropyl)-3-cyano-4-methyl-6-hydroxy-1,2-dihydropiridine-2-one, 1-(dodecyloxypropyl)-3-acetyl-4-methyl-6-hydroxy-1,2-dihydropiridine-2-one, 1-(4-n-octyloxyphenyl)-3-tert-butyl-5-aminopyrazole and the like.

The details thereof are described in JP-A Nos. 4-201483, 7-223367, 7-223368, 7-323660, Japanese Patent Application Nos. 5-278608, 5-297024, 6-18669, 6-18670, 7-316280, 8-027095, 8-027096, 8-030799, 8-12610, 8-132394, 8-358755, 8-358756, 9-069990 and the like.

In the present invention, a compound represented by the above-described general formula (5) is suitably used as the above-described coupler for the purpose of enhancing reactivity of a coupler having low reactivity by combination with a base such as triphenylguanidine.

In the above-described general formula (5), $R^9$ to $R^{12}$ represent a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group.

Among these, it is preferable that at least one of the substituents represented by $R^9$ and $R^{10}$ is an electron attractive group having a Hammett substituent constant $\sigma_p$ of 0.20 or more, and it is more preferable that at least one of $R^9$ and $R^{10}$ is an electron attractive group having a $\sigma_p$ of 0.35 or more.

Preferable examples of electron attractive groups having a $\sigma_p$ of 0.20 or more include, but are not limited to, a cyano group ($\sigma_p$ value is 0.66), perfluoroalkyl groups (for example, a trifluoromethyl group having a $\sigma_p$ of 0.54), acyl groups (for example, an acetyl group having a $\sigma_p$ of 0.50 and a benzoyl group having a $\sigma_p$ of 0.43), a carbamoyl group ($\sigma_p$ value is 0.36) and the like.

As the halogen atom, a fluorine atom, chlorine atom, bromine atom and the like are listed, and among these, a fluorine atom and chlorine atom are more preferable.

The aryl group of substituents $R^9$ to $R^{12}$ may be further substituted by an alkyl group, alkoxy group, aryloxy group, halogen atom, nitro group, cyano group, substituted carbamoyl group, substituted sulfamoyl group, substituted amino group, substituted oxycarbamoyl group, substituted oxysulfonyl group, alkylthio group, arylthio group, alkylsulfonyl group, arylsulfonyl group, aryl group, hydroxy group, acyl group, acyloxy group, substituted sulfonyloxy group, substituted aminocarbonyloxy group or substituted phosphoryloxy group.

As the aryl group, an aryl group having 6 to 30 carbon atoms is preferable, and examples thereof include a phenyl group, 2-methylphenyl group, 2-chlorophenyl group, 2-methoxyphenyl group, 2-ethoxyphenyl group, 2-propoxyphenyl group, 2-isopropoxyphenyl group, 2-butoxyphenyl group, 2-(2-ethylhexyloxy)phenyl group, 2-octyloxyphenyl group, 2-undecyloxyphenyl group, 2-trifluoromethylphenyl group, 2-(2-ethylhexyloxy)-5-chlorophenyl group, 2,2'-hexyloxy-3,5-dichlorophenyl group, 3-(2,4-di-t-pentylphenoxyethoxy)phenyl group, 2-(dibutylaminocarbonylethoxy)phenyl group, 2,4-dichlorophenyl group, 2,5-dichlorophenyl group, 2,4,6-trimethylphenyl group, 3-chlorophenyl group, 3-nitrophenyl group, 3-cyanophenyl group, 3-trifluoromethylphenyl group, 3-methoxyphenyl group, 3-ethoxyphenyl group, 3-butoxyphenyl group, 3-(2'-ethylhexyloxy)phenyl group, 3,4-dichlorophenyl group, 3,5-dichlorophenyl group, 3,4-dimethoxyphenyl group, 3,5-dibutoxyphenyl group, 3-octyloxyphenyl group, 3-(dibutylaminocarbonylmethoxy) phenyl group, 3-(di-2-ethylhexylaminocarbonylmethoxy) phenyl group, 3-dodecyloxyphenyl group, 4-chlorophenyl group, 4-cyanophenyl group, 4-nitrophenyl group, 4-trifluoromethylphenyl group, 4-methoxyphenyl group, 4-ethoxyphenyl group, 4-isopropoxyphenyl group, 4-butoxyphenyl group, 4-(2-ethylhexyloxy)phenyl group, 4-isopentyloxyphenyl group, 4-(octadecyloxy)phenyl group, 4-benzylphenyl group, 4-aminosulfonylphenyl group, 4-N,N'-dibutylsulfonylphenyl group, 4-ethoxycarbonylphenyl group, 4-(2-ethylhexyloxycarbonyl)phenyl group, 4-t-octylphenyl group, 4-fluorophenyl group, 3-acetylphenyl group, 2-acetylaminophenyl group, 2,4-di-t-pentylphenyl group, 4-(2-ethylhexyloxy)carbonylphenyl group, 4-methylthiophenyl group, 4-(4-chlorophenylthio)phenyl group, and in addition, hydroxyphenyl group, phenylsulfonylphenyl group, phenylsulfonyloxyphenyl group, phenylcarbonyloxyphenyl group, dimethylaminocarbonyloxyphenyl group, butylcarbonyloxyphenyl group and the like.

The alkyl group of the substituents $R^9$ to $R^{12}$ may be straight or branched, and may have an unsaturated bond. Further, these alkyl groups may be substituted by an alkoxy group, aryloxy group, alkoxycarbonyl group, aryloxycarbonyl group, aryl group, hydroxy group, halogen atom and the like. Furthermore, this aryl group may be substituted by an alkyl group, alkoxy group, nitro group, cyano group, hydroxy group or halogen atom.

As the alkyl group, an alkyl group having 1 to 30 carbon atoms is preferable, and examples thereof include a methyl group, trifluoromethyl group, ethyl group, butyl group, hexyl group, octyl group, 2-ethylhexyl group, decyl group, dodecyl group, octadecyl group, propyl group, isopropyl group, isobutyl group, sec-butyl group, t-butyl group, pentyl group, 1-ethylpentyl group, cyclopentyl group, cyclohexyl group, isopentyl group, heptyl group, nonyl group, undecyl group, propenyl group, heptadecenyl group, t-octyl group, ethoxyarbonylmethyl group, butoxycarbonylmethyl group, 2-ethylhexyloxycarbonylmethyl group, 1-(ethocarbonyl)ethyl group, 2',4'-diisopentylphenyloxymethyl group, 2',4'-di-t-butylphenyloxymethyl group, ethoxycarbonylethyl group, 2-ethylhexyloxycarbonylethyl group, butyldecyloxycarbonylethyl group, dibutylaminocarbonylmethyl group, dibenzylaminocarbonylethyl group, ethyloxycarbonylpropyl group, 2-ethylheyloxycarbonylpropyl group, 2,4-di-t-amylphenyloxypropyl group, 1-(2',4'-di-t-amylphenyloxy)propyl group, 2,4-di-t-butylphenyloxypropyl group, acetylaminoethyl group, N,N-dihexylaminocarbonylethyl group, 2,4-di-t-amyloxyethyloxycarbonylpropyl group, isostearyloxycarbonylpropyl group, 1-(2,4-di-t-pentylphenyloxy)propyl group, 2,4-di-t-pentylphenyloxyethyloxycarbonylpropyl group, naphthyloxyethyloxycarbonylethyl group, N-methyl-N-phenylethyloxycarbonylethyl group, methanesulfonylaminopropyl group and the like.

The acyl group of the substituents $R^9$ to $R^{12}$ is preferably an acyl group having 2 to 20 carbon atoms, and examples thereof include an acetyl group, propanoyl group, butanoyl group, hexanoyl group, octanoyl group, 2-ethylhexanoyl group, decanoyl group, dodecanoyl group, octadecanoyl group, 2-cyanopropanoyl group, 1,1-dimethylpropanoyl group and the like.

Examples of the substituted carbamoyl group of the substituents $R^9$ to $R^{12}$ include a carbamoyl group, N-alkylcarbamoyl group, N-arylcarbamoyl group, N,N-dialkylcarbamoyl group, N,N-diarylcarbamoyl group, N-alkyl-N-arylcarbamoyl group and the like.

As the substituted carbamoyl group, a substituted carbamoyl group having 1 to 30 carbon atoms is preferable, and examples thereof include a N-methylcarbamoyl group, N-ethylcarbamoyl group, N-propylcarbamoyl group, N-butylcarbamoyl group, N-hexylcarbamoyl group, N-cyclohexylcarbamoyl group, N-octylcarbamoyl group, N-2-ethylhexylcarbamoyl group, N-decylcarbamoyl group, N-octadecylcarbamoyl group, N-phenylcarbamoyl group, N-2-methylphenylcarbamoyl group, N-2-chlorophenylcarbamoyl group, N-2-methoxyphenylcarbamoyl group, N-2-isopropoxyphenylcarbamoyl group, N-2-(2-ethylhexyloxy)phenylcarbamoyl group, N-3-chlorophenylcarbamoyl group, N-3-nitrophenylcarbamoyl group, N-3-cyanophenylcarbamoyl group, N-4-methoxycarbamoyl group, N-4-(2'-ethylhexyloxy)phenylcarbamoyl group, N-4-cyanophenylcarbamoyl group, N-methyl-N-phenylcarbamoyl group, N,N-dimethylcarbamoyl group, N,N-dibutylcarbamoyl group, N,N-diphenylcarbamoyl group, —CONHSO$_2$C$_6$H$_4$CH$_3$—, —CONHSO$_2$N(CH$_3$)Ph, —CONHSO$_2$NHPh and the like.

As the alkoxycarbonyl group of the substituents $R^9$ to $R^{12}$, an alkoxycarbonyl group having 2 to 20 carbon atoms is preferable, and examples thereof include a methoxycarbonyl group, ethoxycarbonyl group, propoxycarbonyl group, butoxycarbonyl group, hexyloxycarbonyl group, 2-ethylhexyloxycarbonyl group, octyloxycarbonyl group, decyloxycarbonyl group, octadecyloxycarbonyl group, phenyloxyethyloxycarbonyl group, phenyloxypropyloxycarbonyl group, 2,4-di-t-amylphenyloxyethylcarbonyl group, 2,6-di-t-butyl-4-methylcyclohexyloxycarbonyl group, isostearyloxycarbonyl group and the like.

As the aryloxycarbonyl group of the substituents $R^9$ to $R^{12}$, an aryloxycarbonyl group having 7 to 30 carbon atoms is preferable, and examples thereof include a 2-methylphenyloxycarbonyl group, 2-chlorophenyloxycarbonyl group, 2,6-dimethylphenyloxycarbonyl group, 2,4,6-trimethylphenyloxycarbonyl group, 2-methoxyphenyloxycarbonyl group, 2-butoxyphenyloxycarbonyl group, 3-cyanophenyloxycarbonyl group, 3-nitrophenyloxycarbonyl group, 2,2-ethylhexylphenyloxycarbonyl group, 3-(2-ethylhexyloxy)phenyoxycarbonyl group, 4-fluorophenyloxycarbonyl group, 4-chlorophenyloxycarbonyl group, 4-cyanophenyloxycarbonyl group, 4-butoxyphenyloxycarbonyl group and the like.

As the acyloxy group of the substituents $R^9$ to $R^{12}$, an acyloxy group having 2 to 20 carbon atoms is preferable, and examples thereof include an acetyloxy group, propanoyl group, butanoyloxy group, pentanoyloxy group, trifluoromethylcarbonyloxy group, octanoyloxy group, decanoyloxy group, undecanoyloxy group, octadecanoyloxy group and the like.

As the alkoxy group of the substituents $R^9$ to $R^{12}$, an alkoxy group having 1 to 30 carbon atoms is preferable, and examples thereof include a methoxy group, ethoxy group, propyloxy group, isopropyloxy group, butoxy group, isobutoxy group, sec-butoxy group, t-butoxy group, pentyloxy group, isopentyloxyl group, hexyloxy group, heptyloxy group, octyloxy group, 2-ethylhexyloxy group, decyloxy group, dodecyloxy group, octadecyloxy group, ethoxycarbonylmethyloxy group, 2-ethylhexyloxycarbonylmethyloxy group, aminocarbonylmethyloxy group, N,N-dibutylaminocarbonylmethyloxy group, N-methylaminocarbonylmethyloxy group, N-ethylaminocarbonylmethyloxyl group, N-octylaminocarbonylmethyloxy group, N-methyl-N-benzylaminocarbonylmethyloxy group, benzyloxy group, cyanomethyloxy group and the like.

As the aryloxy group of the substituents $R^9$ to $R^{12}$, an aryloxy group having 6 to 30 carbon atoms is preferable, and examples thereof include a phenyloxy group, 1-naphthyloxy group, 2-naphthyloxy group, 2-chlorophenyloxy group, 2-methylphenyloxy group, 2-methoxyphenyloxyl group, 2-butoxyphenyloxy group, 3-chlorophenyloxy group, 3-trifluoromethylphenyloxy group, 3-cyanophenyloxy group, 3-(2-ethylhexyloxy)phenyloxy group, 3-nitrophenyloxy group, 4-fluorophenyloxy group, 4-cyanophenyloxy group, 4-butoxyphenyloxy group, 4-(2-ethylhexyloxy)phenyloxy group, 4-octadecylphenyloxy group and the like.

As the alkylthio group of the substituents $R^9$ to $R^{12}$, an alkylthio group having 1 to 30 carbon atoms is preferable, and examples thereof include a methylthio group, ethylthio group, propylthio group, isopropylthio group, butylthio group, isobutylthio group, sec-butylthio group, t-butylthio group, pentylthio group, isopentylthio group, hexylthio group, heptylthio group, octylthio group, 2-ethylhexylthio group, decylthio group, dodecylthio group, octadecylthio group, ethoxycarbonylmethylthio group, 2-ethylhexyloxycarbonylmethylthio group, aminocarbonylmethylthio group, N,N-dibutylaminocarbonylmethyl group, N-methylaminocarbonylmethylthio group, N-ethylaminocarbonylmethylthio group, N-octylaminocarbonylmethylthio group, N-methyl-N-benzylaminocarbonylmethylthio group, benzylthio group, cyanomethylthio group and the like.

As the arylthio group of the substituents $R^9$ to $R^{12}$, an arylthio group having 6 to 30 carbon atoms is preferable, and examples thereof include a phenylthio group, 1-naphthylthio group, 2-naphthylthio group, 2-chlorophenylthio group, 2-methylphenylthio group, 2-methoxyphenylthio group, 2-butoxyphenylthio group, 3-chlorophenylthio group, 3-trifluoromethylphenylthio group. 3-cyanophenylthio group, 3-(2-ethylhexyloxy)phenylthio group, 3-nitrophenylthio group, 4-fluorophenylthio group, 4-cyanophenylthio group, 4-butoxyphenylthio group, 4-(2-ethylhexyloxy)phenylthio group, 4-octadecylphenylthio group and the like.

Examples of the substituted sulfamoyl group of the substituents $R^9$ to $R^{12}$ include a sulfamoyl group, N-alkylsulfamoyl group, N-arylsulfamoyl group, N,N-dialkylsulfamoyl group, N,N-diarylsulfamoyl group and N-alkyl-N-arylsulfamoyl group.

As the substituted sulfamoyl group of the substituents $R^9$ to $R^{12}$, a substituted sulfamoyl group having 0 to 30 carbon atoms is preferable, and examples thereof include a N-methylsulfamoyl group, N-ethylsulfamoyl group, N-propylsulfamoyl group, N-butylsulfamoyl group, N-hexylsulfamoyl group, N-cyclohexylsulfamoyl group, N-octylsulfamoyl group, N-2-ethylhexylsulfamoyl group, N-decylsulfamoyl group, N-octadecylsulfamoyl group, N-phenylsulfamoyl group, N-2-methylphenylsulfamoyl group, N-2-chlorophenylsulfamoyl group, N-2-methoxyphenylsulfamoyl group, N-2-isopropoxyphenylsulfamoyl group, N-2-(2-ethylhexyloxy)phenylsulfamoyl group, N-3-chlorophenylsulfamoyl group, N-3-nitrophenylsulfamoyl group, N-3-cyanophenylsulfamoyl group, N-4-methoxysulfamoyl group, N-4-cyanophenylsulfamoyl group, N-methyl-N-phenylsulfamoyl group, N,N-dimethylsulfamoyl group, N,N-dibutylsulfamoyl group, N,N-diphenylsulfamoyl group, N,N-di-(2-ethylhexyl)sulfamoyl group and the like.

As the alkylsulfonyl group of the substituents $R^9$ to $R^{12}$, an alkylsulfonyl group having 1 to 20 carbon atoms is preferable, and examples thereof include a methylsulfonyl group, ethylsulfonyl group, propylsulfonyl group, isopropylsulfonyl group, butylsulfonyl group, hexylsulfonyl group, cyclohexylsulfonyl group, octylsulfonyl group, 2-ethylhexylsulfonyl group, decanoylsulfonyl group, dodecanoylsulfonyl group, octadecanoylsulfonyl group, cyanomethylsulfonyl group and the like.

As the arylsulfonyl group of the substituents $R^9$ to $R^{12}$, an arylsulfonyl group having 6 to 30 carbon atoms is preferable, and examples thereof include a phenylsulfonyl group, 1-naphthylsulfonyl group, 2-naphthylsulfonyl group, 2-chlorophenylsulfonyl group, 2-methylphenylsulfonyl group, 2-methoxyphenylsulfonyl group, 2-butoxyphenylsulfonyl group, 3-chlorophenylsulfonyl group, 3-trifluoromethylphenylsulfonyl group, 3-cyanophenylsulfonyl group, 3-(2-ethylhexyloxy)phenylsulfonyl group, 3-nitrophenylsulfonyl group, 4-fluorophenylsulfonyl group, 4-cyanophenylsulfonyl group, 4-butoxyphenylsulfonyl group, 4-(2-ethylhexyloxy)phenylsulfonyl group, 4-octadecylphenylsulfonyl group and the like.

As the alkyphosphoryl group of the substituents $R^9$ to $R^{12}$, an alkylphosphoryl group having 2 to 40 carbon atoms is preferable, and examples thereof include a methylphosphoryl group, ethylphosphoryl group, propylphosphoryl group, isopropylphosphoryl group, butylphosphoryl group, isobutylphosphoryl group, sec-butylphosphoryl group, t-butyphosphoryl group, pentylphosphoryl group, isopentylphosphoryl group, hexylphosphoryl group, heptylphosphoryl group, octylphosphoryl group, 2-ethylhexylphosphoryl group, decylphosphoryl group, dodecylphosphoryl group, octadecylphosphoryl group, ethoxycarbonylmethylphosphoryl group, 2-ethylhexyloxycarbonylmethylphosphoryl group, aminocarbonylmethylphosphoryl group, N,N-dibutylaminocarbonylmethylphosphoryl group, N-methylaminocarbonylmethylphosphoryl group, N-ethylaminocarbonylmethylphosphoryl group, N-octylaminocarbonylmethylphosphoryl group, benzylphosphoryl group and the like.

As the arylphosphoryl group of the substituents $R^9$ to $R^{12}$, an arylphosphoryl group having 12 to 50 carbon atoms is preferable, and examples thereof include a phenylphosphoryl group, 1-naphthylphosphoryl group, 2-nathphylphosphoryl group, 2-chlorophenylphosphoryl group, 2-methylphenylphosphoryl group, 2-methoxyphenylphosphoryl group, 2-butoxyphenylphosphoryl group, 3-chlorophenylphosphoryl group, 3-trifluoromethylphenylphosphoryl group, 3-cyanophenylphosphoryl group, 3-(2-ethylhexyloxy)phenylphosphoryl group, 3-nitrophenylphosphoryl group, 4-butoxyphenylphosphoryl group, 4-(2-ethylhexyloxy)phenylphosphoryl group, 4-octadecylphenylphosphoryl group and the like.

Examples of the substituted amino group of the substituents $R^9$ to $R^{12}$ include an amino group, N-alkylamino group, N-arylamino group, N-acrylamino group, N-sulfonylamino group, N,N-dialkylamino group, N,N-diarylamino group, N-alkyl-N-arylamino group, N,N-disulfonylamino group and the like.

As the substituted amino group, a substituted amino group having 0 to 50 carbon atoms is preferable, and examples thereof include a N-methylamino group, N-ethylamino group, N-propylamino group, N-isopropylamino group, N-tert-butylamino group, N-hexylamino group, N-cyclohexylamino group, N-octylamino group, N-2-ethylhexylamino group, N-decylamino group, N-octadecylamino group, N-benzylamino group, N-phenylamino group, N-2-methylphenylamino group, N-2-chlorophenylamino group, N-2-methoxyphenylamino group, N-2-isopropoxyphenylamino group, N-2-(2-ethylhexyloxy)phenylamino group, N-3-chlorophenylamino group, N-3-nitrophenylamino group, N-3-cyanophenylamino group, N-4-methoxyamino group, N-4-(2'-ethylhexyloxy)phenylamino group, N-4-cyanophenylamino group, N-methyl-N-phenylamino group, N,N-dimethylamino group, N,N-dibutylamino group, N,N-diphenylamino group, N,N-diacetylamino group, N,N-dibenzoylamino group, N,N-(dibutylcarbonyl)amino group, N,N-(di-2-ethylhexylcarbonyl)amino group, N,N-(dimethylsulfonyl)amino group, N,N-(diethylsulfonyl)amino group, N,N-(dibutylsulfonyl)amino group, N,N-(2-ethylhexylsulfonyl)amino group, N,N-(diphenylsulfonyl)amino group and the like.

Typical examples of a pyrrolopyrimidine compound represented by the above-described general formula (5) suitably used as a coupler in the present invention are listed below although the present invention is not limited to these. Substituents used in exemplary compounds are described below in order, and combinations thereof are shown in Tables 1 and 2. The numerical value in $R^9$ to $R^{12}$ columns in Tables 1 and 2 represents the number of a substituent.

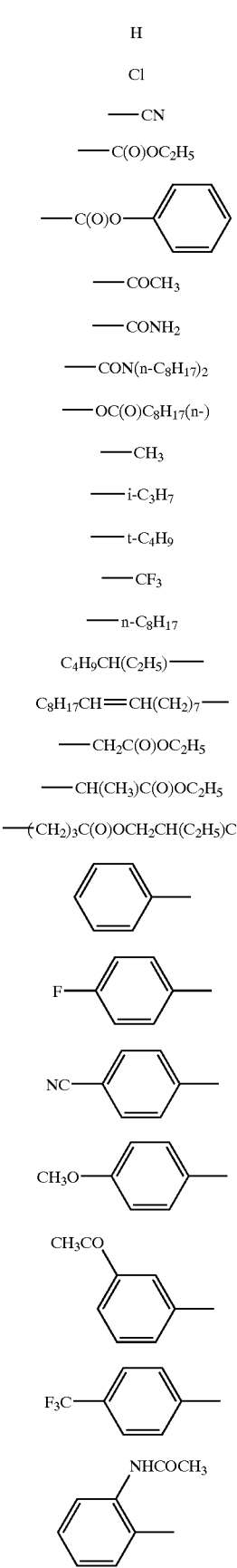
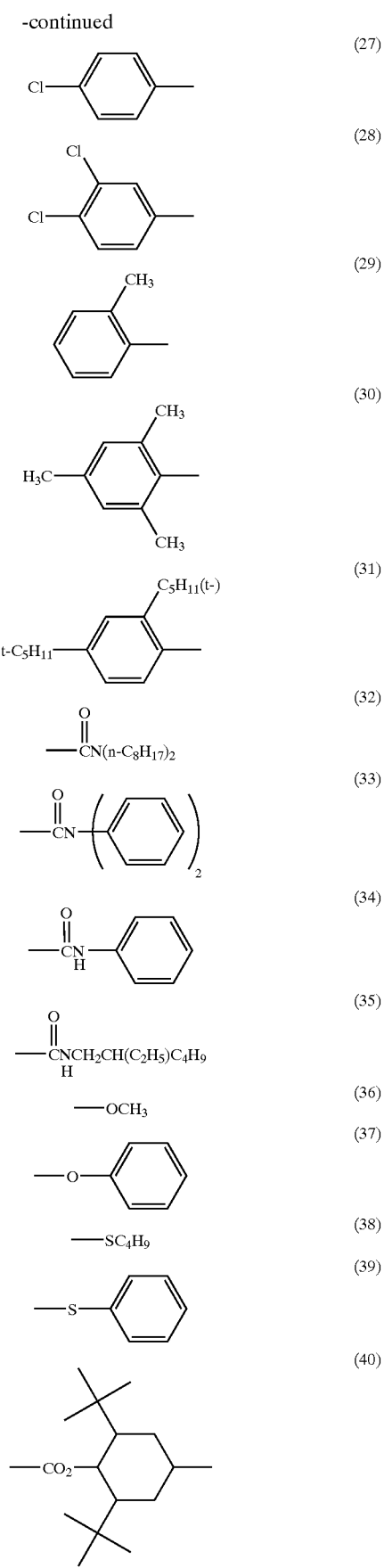

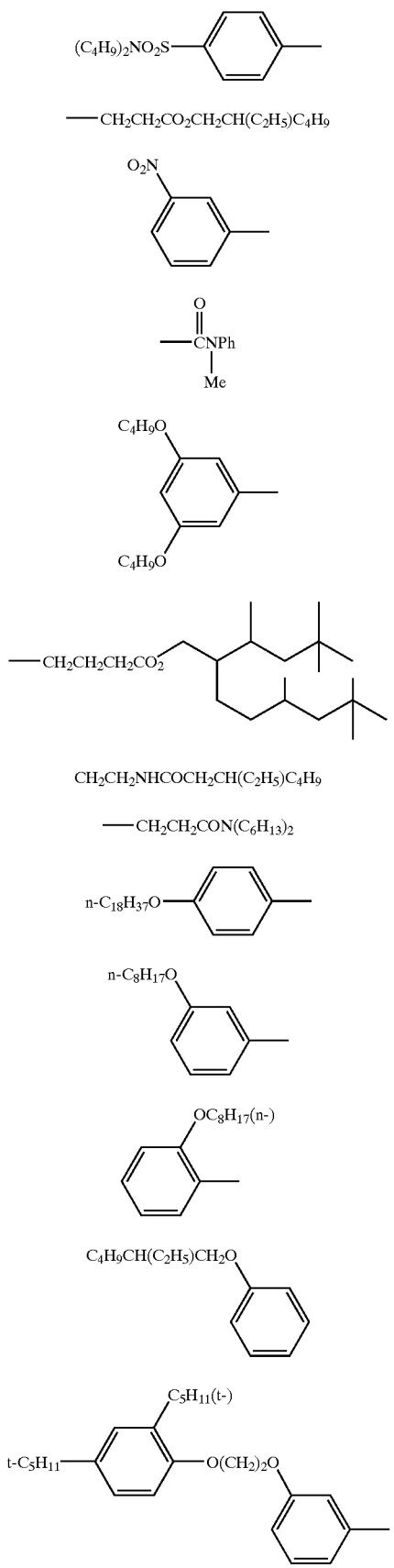
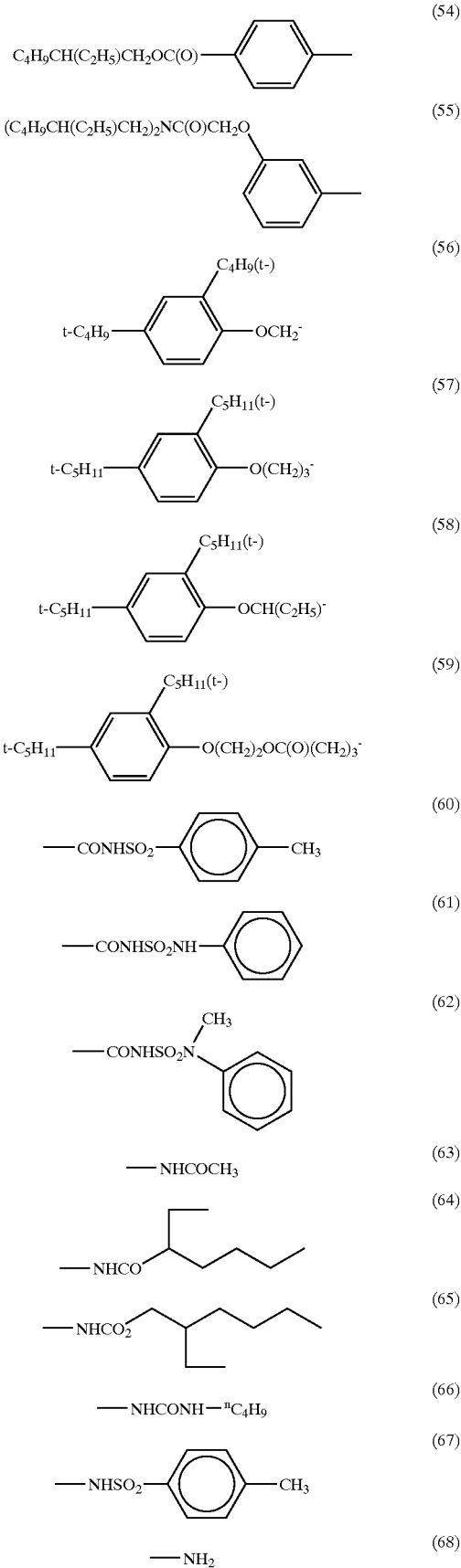

-continued

(69)
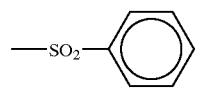

TABLE 1

| Coupler No. | $R^9$ | $R^{10}$ | $R^{11}$ | $R^{12}$ |
|---|---|---|---|---|
| (1) | (20) | (3) | (1) | (1) |
| (2) | (20) | (3) | (10) | (1) |
| (3) | (20) | (3) | (10) | (2) |
| (4) | (20) | (3) | (10) | (10) |
| (5) | (20) | (4) | (10) | (20) |
| (6) | (4) | (4) | (10) | (1) |
| (7) | (4) | (3) | (20) | (1) |
| (8) | (5) | (3) | (10) | (1) |
| (9) | (6) | (3) | (15) | (1) |
| (10) | (7) | (3) | (12) | (1) |
| (11) | (8) | (3) | (10) | (1) |
| (12) | (9) | (3) | (10) | (1) |
| (13) | (10) | (3) | (16) | (1) |
| (14) | (10) | (3) | (13) | (1) |
| (15) | (11) | (3) | (20) | (1) |
| (16) | (20) | (3) | (16) | (1) |
| (17) | (20) | (3) | (14) | (10) |
| (18) | (17) | (3) | (20) | (1) |
| (19) | (20) | (3) | (17) | (1) |
| (20) | (20) | (3) | (56) | (1) |
| (21) | (20) | (3) | (19) | (1) |
| (22) | (20) | (3) | (59) | (1) |
| (23) | (20) | (3) | (57) | (1) |
| (24) | (52) | (3) | (58) | (1) |
| (25) | (52) | (3) | (57) | (1) |
| (26) | (20) | (3) | (16) | (1) |
| (27) | (20) | (3) | (15) | (10) |
| (28) | (20) | (3) | (15) | (2) |
| (29) | (18) | (3) | (20) | (1) |
| (30) | (21) | (3) | (16) | (1) |

TABLE 2

| Coupler No. | $R^9$ | $R^{10}$ | $R^{11}$ | $R^{12}$ |
|---|---|---|---|---|
| (31) | (22) | (3) | (16) | (1) |
| (32) | (20) | (3) | (28) | (1) |
| (33) | (24) | (3) | (13) | (2) |
| (34) | (25) | (3) | (10) | (10) |
| (35) | (26) | (3) | (10) | (20) |
| (36) | (30) | (3) | (13) | (1) |
| (37) | (31) | (3) | (13) | (1) |
| (38) | (27) | (3) | (49) | (1) |
| (39) | (20) | (3) | (50) | (1) |
| (40) | (54) | (3) | (10) | (1) |
| (41) | (20) | (3) | (53) | (1) |
| (42) | (20) | (3) | (52) | (1) |
| (43) | (20) | (3) | (51) | (1) |
| (44) | (25) | (3) | (16) | (1) |
| (45) | (52) | (3) | (13) | (1) |
| (46) | (53) | (3) | (13) | (1) |
| (47) | (27) | (3) | (16) | (10) |
| (48) | (27) | (3) | (57) | (1) |
| (49) | (28) | (3) | (55) | (1) |
| (50) | (28) | (3) | (16) | (1) |
| (51) | (29) | (3) | (16) | (1) |
| (52) | (29) | (38) | (10) | (1) |
| (53) | (29) | (34) | (16) | (1) |
| (54) | (29) | (35) | (10) | (1) |
| (55) | (29) | (3) | (10) | (20) |
| (56) | (20) | (3) | (46) | (1) |
| (57) | (22) | (32) | (10) | (1) |
| (58) | (20) | (3) | (10) | (36) |
| (59) | (20) | (40) | (10) | (1) |
| (60) | (20) | (3) | (10) | (38) |
| (61) | (20) | (3) | (64) | (1) |

TABLE 2-continued

| Coupler No. | $R^9$ | $R^{10}$ | $R^{11}$ | $R^{12}$ |
|---|---|---|---|---|
| (62) | (27) | (40) | (64) | (1) |
| (63) | (27) | (40) | (68) | (60) |
| (64) | (28) | (40) | (68) | (61) |
| (65) | (27) | (35) | (62) | (1) |
| (66) | (28) | (34) | (68) | (61) |
| (67) | (20) | (69) | (65) | (1) |

The pyrrolopyrimidine compounds represented by the general formula (5) may be used alone or in combination of two or more.

The pyrrolopyrimidine compounds represented by the general formula (5) can be synthesized by known methods, and an example of the synthesis of an exemplary coupler (specific compound (16)) is shown below.

Synthesis Example

Synthesis of specific compound (16)

2-amino-3-cyano-4-phenylpyrrole was obtained by condensing a hydrochloride of 2-aminoacetophenone and malononitrile in the presence of an alkali. Then, 18.3 g of this 2-amino-3-cyano-4-phenylpyrrole, 52.2 g of methyl 9,10-heptadecenylcarbonylacetate and 23.9 g of ammonium acetate were dispersed in 100 ml of toluene, and heated to reflux for 3 hours. After cooling, acetonitrile was added, and a crystal precipitated was filtered off before being washed with water and methanol to obtain 29.8 g of an intended compound (specific compound (16)).

The amount added of the coupler is from 0.02 to 5 $g/m^2$, and preferably from 0.1 to 4 $g/m^2$ in the heat sensitive recording layer.

An amount less than 0.02 $g/m^2$ is not preferable, in consideration of the color developing property, and an amount over 5 $g/m^2$ is not preferable in consideration of the suitability thereof for coating.

The coupler in the present invention can be compounded with a water-soluble polymer added together with other components and dispersed in solid form for use by a sand mill and the like, although it can also be emulsified with a suitable emulsifying aid for use. The solid dispersion method and the emulsification method are not particularly restricted, and conventionally known methods can be used. The details of these methods are described in JP-A Nos. 59-190886, 2-141279 and 7-17145.

The diazonium salt compound used in the present invention is represented by the following general formula:

$$Ar-N_2^+ \cdot X^-$$

(wherein, Ar represents an aromatic moiety, and $X^-$ represents an acid anion), and causes a coupling reaction with a coupler and develops color by heating and is decomposed by light. In these compounds, the maximum absorption wavelength can be controlled by the position and type of the substituent in the Ar moiety.

Specific examples of a diazonium forming a salt include 4-(p-tolylthio)-2,5-dibutoxybenzenediazonium, 4-(4-chlorophenylthio)-2,5-dibutoxybenzenediazonium, 4-(N,N-dimethylamino)benzenediazonium, 4-(N,N-diethylamino) benzenediazonium, 4-(N,N-dipropylamino) benzenediazonium, 4-(N-methyl-N-benzylamino) benzenediazonium, 4-(N,N-dibenzylamino) benzenediazonium, 4-(N-ethyl-N-hydroxyethylamino)

benzenediazonium, 4-(N,N-diethylamino)-3-methoxybenzenediazonium, 4-(N,N-dimethylamino)-2-methoxybenzenediazonium, 4-(N-benzoylamino)-2,5-diethoxybenzenediazonium, 4-morpholino-2,5-dibutoxybenzenediazonium, 4-anilinobenzenediazonium, 4-[N-(4-methoxybenzoyl)amino]-2,5-diethoxybenzenediazonium, 4-pyrrolidino-3-ethylbenzenediazonium, 4-[N-(1-methyl-2-(4-methoxyphenoxy)ethyl)-N-hexylamino]-2-hexyloxybenzenediazonium, 4-[N-(2-(4-methoxyphenoxy)ethyl)-N-hexylamino]-2-hexyloxybenzenediazonium, 2-(1-ethylpropyloxy)-4-[di-(di-n-butylaminocarbonylmethyl)amino]benzenediazonium and the like.

The maximum absorption wavelength λmax of the diazonium salt compound used in the present invention is preferably 450 nm or less from the standpoint of its effect, and more preferably from 290 to 440 nm. It is not preferable that the diazonium salt compound has λmax longer than the above-described wavelength range from the standpoint of storage stability before use, and it is not preferable that the diazonium salt compound has λmax shorter than the above-described wavelength range from the standpoint of the image fixing property, the image storability and the hue from violet to cyan when combined with a coupler.

Further, it is preferable that the diazonium salt compound use in the present invention has 12 or more carbon atoms, has a solubility in water of 1% or less and a solubility in ethyl acetate of 5% or more.

Of these diazonium salt compounds, at least one selected from compounds represented by the above-described general formula (6), compounds represented by the above-described general formula (7) and compounds represented by the above-described general formula (8) is preferably used from the standpoints of the hue of the dye, image storability and image fixing property.

In the general formula (6), Ar represents a substituted or unsubstituted aryl group. As the substituent, an alkyl group, alkoxy group, alkylthio group, aryl group, aryloxy group, arylthio group, acyl group, alkoxycarbonyl group, carbamoyl group, carbamide group, sulfonyl group, sulfamoyl group, sulfonamide group, ureide group, halogen group, amino group, heterocyclic group and the like are listed, and these substituents may be further substituted.

An aryl group having 6 to 30 carbon atoms is preferable as the aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may be substituted by an alkyloxy group, alkylthio group, substituted phenyl group, cyano group, substituted amino group, halogen atom, heterocyclic group and the like.

$R^{13}$ and $R^{14}$ represent a substituted or unsubstituted alkyl group or a substituted or unsubstituted aryl group. $R^{13}$ and $R^{14}$ may be the same or different.

Examples of the substituent include, but are not limited to, an alkoxy group, alkoxycarbonyl group, alkylsulfonyl group, substituted amino group, substituted amide group, aryl group, aryloxy group and the like.

The above-described alkyl group is preferably an alkyl group having 1 to 18 carbon atoms, and preferable examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino) ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

An aryl group having 6 to 30 carbon atoms is preferable as the above-described aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may be substituted by an alkyloxy group, alkylthio group, substituted phenyl group, cyano group, substituted amino group, halogen atom, heterocyclic group and the like.

In the above-described general formula (7), $R^{16}$, $R^{17}$ and $R^{18}$ represent a substituted or unsubstituted alkyl group or a substituted or unsubstituted aryl group. $R^{16}$, $R^{17}$ and $R^{18}$ may be the same or different. Examples of the substituent include an alkyl group, alkoxy group, alkylthio group, aryl group, aryloxy group, arylthio group, acyl group, alkoxycarbonyl group, carbamoyl group, carbamide group, sulfonyl group, sulfamoyl group, sulfonamide group, ureide group, halogen atom, amino group, heterocyclic group and the like.

An alkyl group having 1 to 18 carbon atoms is preferable as the above-described alkyl group, and preferable examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group, 1-methyl-2-(4-methoxyphenoxy)ethyl group, di-n-butylaminocarbonylmethyl group, di-n-octylaminocarbonylmethyl group and the like.

An aryl group having 6 to 30 carbon atoms is preferable as the above-described aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may be substituted by an alkyloxy group, alkylthio group, substituted phenyl group, cyano group, substituted amino group, halogen atom, heterocyclic group and the like.

Y represent a hydrogen atom or —$OR^{15}$ group.

In —$OR^{15}$, $R^{15}$ represents a substituted or unsubstituted alkyl group or a substituted or unsubstituted aryl group.

Examples of the substituent include an alkyl group, alkoxy group, alkylthio group, aryl group, aryloxy group, arylthio group, acyl group, alkoxycarbonyl group, carbamoyl group, carbamide group, sulfonyl group, sulfamoyl group, sulfonamide group, ureide group, halogen atom, amino group, heterocyclic group and the like.

Among these, Y is preferably a hydrogen atom or an alkoxy group in which $R^{15}$ is an alkyl group from the standpoint of hue adjustment.

An alkyl group having 1 to 18 carbon atoms is preferable as the above-described alkyl group, and preferable examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

An aryl group having 6 to 30 carbon atoms is preferable as the above-described aryl group, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may be substituted by an alkyloxy group, alkylthio group, substituted phenyl group, cyano group, substituted amino group, halogen atom, heterocyclic group and the like.

In the above-described general formula (8), $R^{19}$ and $R^{20}$ represent a substituted or unsubstituted alkyl group or a substituted or unsubstituted aryl group. $R^{19}$ and $R^{20}$ may be the same or different.

Examples of the substituent include an alkyl group, alkoxy group, alkylthio group, aryl group, aryloxy group, arylthio group, acyl group, alkoxycarbonyl group, carbamoyl group, carbamide group, sulfonyl group, sulfamoyl group, sulfonamide group, ureide group, halogen atom, amino group, heterocyclic group and the like.

As the above-described alkyl group, an alkyl group having 1 to 18 carbon atoms is preferable, and preferable examples thereof include a methyl group, trifluoromethyl group, ethyl group, propyl group, isopropyl group, butyl group, sec-butyl group, t-butyl group, pentyl group, isopentyl group, cyclopentyl group, hexyl group, cyclohexyl group, octyl group, t-octyl group, 2-ethylhexyl group, nonyl group, octadecyl group, benzyl group, 4-methoxybenzyl group, triphenylmethyl group, ethoxycarbonylmethyl group, butoxycarbonylmethyl group, 2-ethylhexyloxycarbonylmethyl group, 2',4'-diisopentylphenyloxymethyl group, 2',4'-di-t-butylphenyloxymethyl group, dibenzylaminocarbonylmethyl group, 2,4-di-t-amylphenyloxypropyl group, ethoxycarbonylpropyl group, 1-(2',4'-di-t-amylphenyloxy)propyl group, acetylaminoethyl group, 2-(N,N-dimethylamino)ethyl group, 2-(N,N-diethylamino)propyl group, methanesulfonylaminopropyl group, acetylaminoethyl group, 2-(N,N-dimethylamino)ethyl group, 2-(N,N-diethylamino)propyl group and the like.

As the above-described aryl group, an aryl group having 6 to 30 carbon atoms is preferable, and examples thereof include, but are not limited to, a phenyl group, 2-methylphenyl group, 2-chlorophenyl group, 2-methoxyphenyl group, 2-butoxyphenyl group, 2-(2-ethylhexyloxy)phenyl group, 2-octyloxyphenyl group, 3-(2,4-di-t-pentylphenoxyethoxy)phenyl group, 4-chlorophenyl group, 2,5-dichlorophenyl group, 2,4,6-trimethylphenyl group, 3-chlorophenyl group, 3-methylphenyl group, 3-methoxyphenyl group, 3-butoxyphenyl group, 3-cyanophenyl group, 3-(2-ethylhexyloxy)phenyl group, 3,4-dichlorophenyl group, 3,5-dichlorophenyl group, 3,4-dimethoxyphenyl group, 3-(dibutylaminocarbonylmethoxy)phenyl group, 4-cyanophenyl group, 4-methylphenyl group, 4-methoxyphenyl group, 4-butoxyphenyl group, 4-(2-ethylhexyloxy)phenyl group, 4-benzylphenyl group, 4-aminosulfonylphenyl group, 4-N,N-dibutylaminosulfonylphenyl group, 4-ethoxycarbonylphenyl group, 4-(2-ethylhexylcarbonyl)phenyl group, 4-fluorophenyl group, 3-acetylphenyl group, 2-acetylaminophenyl group, 4-(4-chlorophenylthio)phenyl group, 4-(4-methylphenyl)thio-2,5-butoxyphenyl group, 4-(N-benzyl-N-methylamino)-2-dodecyloxycarbonylphenyl group and the like. Further, these groups may be substituted by an alkyloxy group, alkylthio group, substituted phenyl group, cyano group, substituted amino group, halogen atom, heterocyclic group and the like.

In compounds represented by the above-described general formula (6), compounds represented by the above-described general formula (7) and compounds represented by the above-described general formula (8), X⁻ represents an acid anion.

As this acid anion, a polyfluoroalkylcarboxylic acid having 1 to 9 carbon atoms, a polyfluoroalkylsulfonic acid having 1 to 9 carbon atoms, boron tetrafluoride, tetraphenylboric acid, hexafluorophosphoric acid, aromatic carboxylic acid, aromatic sulfonic acid and the like are listed. Among these, hexafluorophosphoric acid is preferable from the standpoint of crystallinity.

Specific examples of compounds represented by the above-described general formula (6), compounds represented by the above-described general formula (7) and compounds represented by the above-described general formula (8) are listed below, but the present invention is not limited to these.

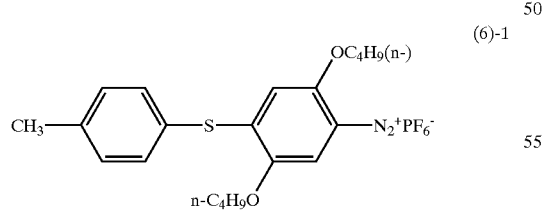
(6)-1

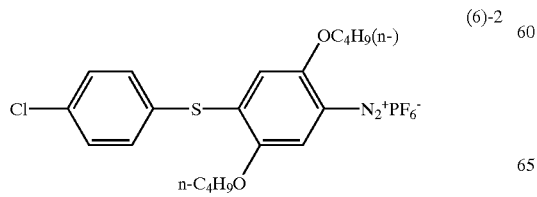
(6)-2

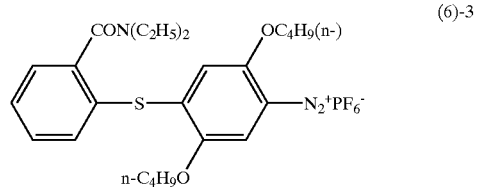
(6)-3

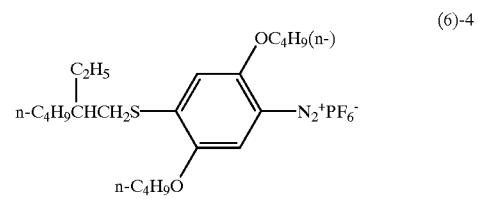
(6)-4

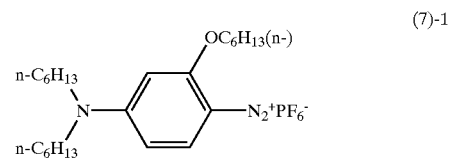
(7)-1

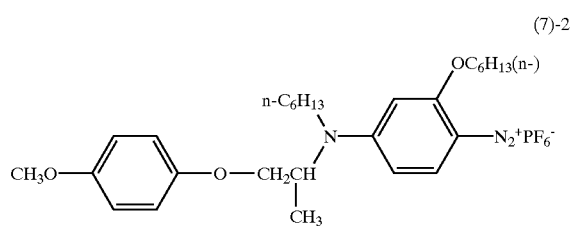
(7)-2

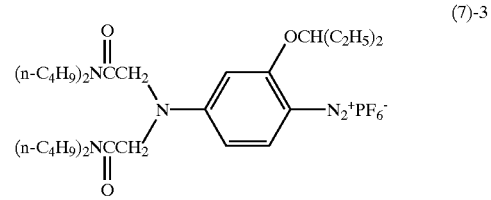
(7)-3

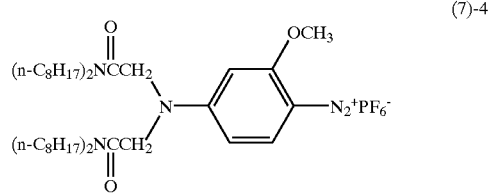
(7)-4

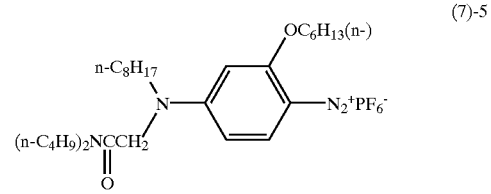
(7)-5

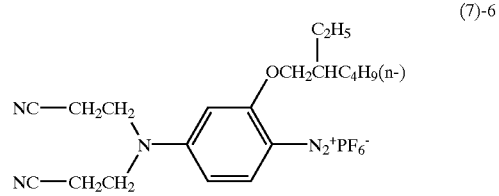
(7)-6

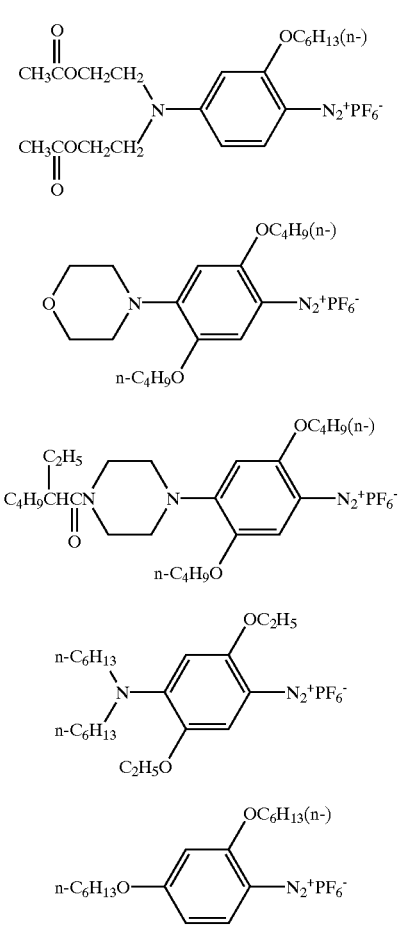

In the present invention, at least one compound selected from compounds represented by the above-described general formula (6), compounds represented by the above-described general formula (7) and compounds represented by the above-described general formula (8) may be used or two or more compounds may be used in combination. Further, at least one compound selected from compounds represented by the above-described general formula (6), compounds represented by the above-described general formula (7) and compounds represented by the above-described general formula (8) may be used together with an ordinary diazonium salt compound in accordance with various objectives such as hue adjustment and the like.

The amount of the diazonium salt compound used in the present invention contained in the heat sensitive recording layer is preferably from 0.02 to 3 g/m$^2$, and more preferably from 0.1 to 2 g/m$^2$.

It is preferable that the diazonium salt compound used in the present invention is contained in a microcapsule from the standpoint of storability.

The method for encapsulation is not particularly restricted, and can be effected by a conventionally known method using a wall material such as gelatine, polyurea, polyurethane, polyimide, polyester, polycarbonate, melamine and the like. The details of the microcapsulation are described in JP-A No. 2-141279 and the like. Further, an organic solvent having a high boiling point may be used as a solvent for dispersing a diazonium salt compound in microcapsulation. This organic solvent is not particularly restricted, and conventionally known compounds such as alkyl phthalate, phosphate, citrate, benzoate, alkylamide, fatty ester, trimesate and the like can be used. The details thereof are described in JP-A No. 7-17145.

In the present invention, a color developing aid can be added for the purpose of promoting a color developing reaction in addition to a guanidine base and a coupler according to the present invention. As such a color developing aid, phenol derivatives, naphthol derivatives, alkoxy-substituted benzenes, alkoxy-substituted naphthalense, hydroxy compounds, carbonic amide compounds, sulfonic amide compounds and the like are listed. It is believed that these compounds decrease the melting point of a coupler or a basic substance, or increase heat penetration property of wall of a microcapsule leading to high color developing density.

The heat sensitive recording material of the present invention is produced by preparing a coating solution comprising the guanidine base of the present invention, a diazonium salt compound, a coupler and other additives, applying the coating solution on a substrate such as paper, synthetic resin film and the like by a coating method such as bar coating, blade coating, air knife coating, gravure coating, roll coating, spray coating, dip coating, curtain coating and the like and drying the solution to provide a heat sensitive recording layer having a solid content of 2 to 30 g/m$^2$.

The binder used in the present invention is not particularly restricted, and conventionally known binders can be used such as polyvinyl alcohol, hydroxyethylcellulose, methylcellulose, carboxymethylcellulose, gelatin, styrene-acrylic acid copolymer and the like. The details thereof are described in JP-A No. 2-141279 and the like. In addition, various organic or inorganic pigments, various stabilizers, antioxidants and the like may be added if required.

A heat sensitive recording material of the present invention, a guanidine base, diazonium salt compound, coupler and the like may be contained in the same layer as in the above-described method, or a laminated structure can be adopted in which these compounds are contained in separate layers.

As the substrate used in the present invention, conventionally known substrates can be used. Specifically, neutral paper, acidic paper, recycled paper, polyolefin resin-laminated paper, synthetic paper, polyester films, cellulose derivative films such as triacetic acid cellulose film and the like, polystyrene films, polyolefin films such as polypropylene film and polyethylene film, and the like. These may be used alone or in combination.

The thickness of the above-described substrate is from 20 to 200 μm. Further, an intermediate layer can also be provided between the substrate and the heat sensitive recording layer. This is described in JP-A No. 61-54980 and the like.

In the heat sensitive recording material of the present invention, it is preferable that a protective layer is laminated on the heat sensitive recording layer. This protective layer is constituted of a water-soluble polymer compound, pigment and the like. A compound having an ultraviolet ray transmittance-controlling function is preferably contained in this protective layer from the standpoint of compatibility of light resistance and light fixing property. This heat sensitive recording material comprising a compound having an ultraviolet ray transmittance-controlling function is described in JP-A No. 7-276808 in detail.

The heat sensitive recording material of the present invention can be applied as a multicolor heat sensitive recording material. This multicolor heat sensitive recording material (heat sensitive recording material) is described in JP-A No.

4-135787, 4-144784, 4-144785, 4-194842, 4-247447, 4-247448, 4-340540, 4-340541, 5-34860 and the like. Specifically, it can be obtained by laminating heat sensitive recording layers developing different hues. The layer structure is not particularly restricted, and there is listed as one example a multicolor heat sensitive recording material in which a two-layer (layers B and C) heat sensitive recording layer comprising a combination of two kinds of diazonium salt compounds having different photo-sensitive wavelengths with couplers which develop different hues when reacted under heat with the respective diazonium salt compounds is laminated with a heat sensitive recording layer (layer A) comprising a combination of an electron donative colorless dye with an electron receptive compound. Specifically, it has, on a substrate, a first heat sensitive recording layer (layer A) containing an electron donative colorless dye and an electron receptive compound, a second layer (layer B) containing a diazonium salt compound having a maximum absorption wavelength of 360±20 nm and a coupler which develops color when reacted under heat with the diazonium salt compound, and a third layer (layer C) comprising a diazonium salt compound having a maximum absorption wavelength of 400±20 nm and a coupler which develops color when reacted under heat with the diazonium salt compound. In this example, if the developing hues of the respective heat sensitive recording layers are selected to be yellow, magenta and cyan, namely the three primary colors in color subtractive mixing, full color image recording becomes possible.

For conducting recording using this multicolor heat sensitive recording material, the third heat sensitive recording layer (layer C) is first heated to allow a diazonium salt and a coupler contained in the layer to develop color. Subsequently, any unreacted diazonium salt compound contained in the layer C is decomposed and fixed by irradiation with light of 400±20 nm, then, sufficient heat for color development of the second heat sensitive recording layer (layer B) is imparted for allowing the diazonium salt compound and the coupler contained in this layer to develop color. In this operation, the layer C is also heated intensely, however, since the diazonium salt compound therein is already decomposed (fixed with light) and no color developing ability remains, the layer does not develop color. Further, the diazonium salt compound contained in the layer B is decomposed by irradiation with light of 360±20 nm, and finally, sufficient heat is imparted for allowing the first heat sensitive layer (layer A) to develop color. In this operation, the layers C and B are also heated intensely, however, since the diazonium salt compounds therein are already decomposed and no color developing ability remains, the layers do not develop color.

Further, it is also possible for any of heat sensitive layers (layer A, layer B and layer C in order from upper side) constituted of a heat sensitive layer comprising a combination of three kinds of diazonium salt compounds having different photo-sensitive wavelengths with couplers which develop different hues when reacted under heat with the respective diazonium salt compounds. In particular, such a layer structure is required when intending to enhance the image quality by making the yellow layer, which has a lower visual sensitivity, the lowest layer in order to reduce the influence on image quality of the roughness of the surface of the substrate. When all heat sensitive layers (layer A, layer B and layer C) are diazo-based heat sensitive layers, layer A and layer B should be fixed with light after color development. Layer C is not required to be subjected to light fixation.

As a light source for fixation used in the above-described light fixation, various fluorescent lamps, xenon lamps, mercury lamps and the like are used. It is preferable that the light emission spectrum corresponds approximately to the absorption spectrum of the diazonium salt compound used in the heat sensitive recording material since then efficient light fixation is possible.

When recording on a heat sensitive recording material of the present invention, it is also possible for the recording material to be used as a thermal developing type heat sensitive material in which the material is exposed through an original sheet to decompose the diazonium salt compound in places other than image formation parts and form a latent image. The whole material is then thermally developed by heating heated and an image obtained.

The following examples further illustrate the present invention in detail, but do not limit the scope thereof. In the examples, all "parts" are by weight.

First, an example of the synthesis of a guanidine compound of the present invention is shown below.

Synthesis of the Guanidine Compound of Specific Example (1)-3

150 g of m-hydroxyacetanilide, 101 g of 1,3-dibromopropane and 210 g of potassium carbonate were added to 1.2 liters of N,N-dimethylacetamide, and reacted for 3 hours while the inner temperature (the temperature of the reaction mixture in the reaction vessel) was kept at 85° C. After the completion of the reaction, the reaction mixture was poured into ice water, and the precipitated crystals were filtered to obtain crystals of 1,3-bis(m-acetamidephenyloxy) propane.

This crystal was dried for one day at 50° C., then added to a solution prepared by dissolving 300 g of concentrated hydrochloric acid in 1 liter of ethanol, and the mixture was heated for 2 hours at reflux temperature. This reaction mixture was poured into ice water, and to this was added an aqueous sodium hydroxide solution to make the mixture weakly alkaline. The precipitated crystal was filtered, washed with cool methanol to obtain 206 g of 1,3-bis(m-aminophenyloxy)propane.

206 g of N,N'-dicyclohexylcarbodiimide and 129 g of 1,3-bis(m-aminophenyloxy)propane were mixed with 500 ml of toluene, and to this was aded 4 g of aluminum chloride in several portions at room temperature.

Upon completion of the heat generation, 1 liter of methanol and 20 g of activated carbon was added to the mixture which was then stirred for 1 hour while the inner temperature was kept at 50° C. The reaction solution was filtered to remove solids, about a half amount of methanol was distilled off under reduced pressure, and the residue was cooled until the inner temperature reached 5° C. The precipitated crystal was filtered and dried to obtain 283 g of crystals of the guanidine compound of Specific Example (1)-3.

Identification of the guanidine compound of Specific Example (1)-3 was conducted using $^1$H-NMR (solvent: DMSO-$d_6$, 300 MHz) Data are shown below.

$^1$H-NMR (δ, ppm) 0.98 to 1.26 (m, 20 H), 1.54 (m, 4 H), 1.60 (m, 8 H), 1.79 (m, 8 H), 2.11 (t, 2 H), 3.36 (m, 4 H), 4.04 (t, 4 H), 4.74 (d, 4 H), 6.22 to 6.29 (m, 4 H), 6.37 (d, 2 H), 7.03 (t, 2 H)

Synthesis of Guanidine Compound of Specific Example (1)-1

1,3-Bis(m-aminophenyloxy)propane was obtained in the same manner as in the case of a guanidine compound of Specific Example (1)-3.

206 g of N,N'-dicyclohexylcarbodiimide and 129 g of 1,3-bis(m-aminophenyloxy)propane were mixed with 500 ml of toluene, and to this was added 4 g of aluminum chloride in several portions at room temperature.

Upon completion of the heat generation, to this was added 0.8 liters of methanol and 20 g of activated carbon, and the mixture was stirred for 1 hour while the inner temperature was kept at 50° C. The reaction solution was filtered to remove solids, about 0.5 liters of methanol was distilled off under reduced pressure, and the residue was cooled until the inner temperature reached 5° C. The precipitated crystals were filtered and dried to obtain 251 g of crystals of the guanidine compound of Specific example (1)-1.

Identification of the guanidine compound of Specific Example (1)-1 was conducted using $^1$H-NMR (solvent: DMSO-$d_6$, 300 MHz). Data are shown below.

$^1$H-NMR (δ, ppm): 0.98 to 1.26 (m, 20 H), 1.32 (d, 3 H), 1.54 (m, 4 H), 1.60 (m, 8 H), 1.78 (m, 8 H), 3.38 (m, 4 H), 4.00 (m, s H), 4.67 (m, 1 H), 4.80 (m, 4 H), 6.23 to 6.31 (m, 4 H), 6.38 (t, 2 H), 7.02 (t, 2 H)

Synthesis of Guanidine Compound of Specific Example (4)-5

206 g of N,N'-dicyclohexylcarbodiimide and 100 g of 4,4'-diaminodiphenyl ether were mixed with 500 ml of toluene, and to this was added 4 g of aluminum chloride in several portions at room temperature.

Upon completion of the heat generation, to this was added 1 liter of methanol and 20 g of activated carbon, and the mixture was stirred for 1 hour while keeping the inner temperature at 50° C. The reaction solution was filtered to remove solids, about 0.3 liters of methanol was distilled off under reduced pressure, and the residue was cooled until the inner temperature reached 10° C. The precipitated crystal was filtered and dried to obtain 298 g of crystals of the guanidine compound of Specific example (4)-5.

Identification of the guanidine compound of Specific Example (4)-5 was conducted using $^1$H-NMR (solvent: DMSO-$d_6$, 300 MHz). Data are shown below.

$^1$H-NMR (δ, ppm): 0.97 to 1.28 (m, 20 H), 1.56 (m, 4 H), 1.63 (m, 8 H), 1.81 (m, 8 H), 3.37 (m, 4 H), 4.71 (d, 4 H), 6.63 (d, 4 H), 6.78 (d, 4 H)

Synthesis of Guanidine Compound of Specific Example (2)-4

206 g of N,N'-dicyclohexylcarbodiimide and 71 g of 2,4-diaminodichlorobenzene were mixed with 500 ml of toluene, and to this was added 3 g of aluminum chloride in several portions at room temperature.

Upon completion of the heat generation, to this was added 1 liter of methanol and 20 g of activated carbon, and the mixture was stirred for 1 hour while the inner temperature was kept at 50° C. The reaction solution was filtered to remove solids, about 0.3 liters of methanol was distilled off under reduced pressure, and the residue was cooled until the inner temperature reached 10° C. The precipitated crystals were filtered and dried to obtain 183 g of crystals of the guanidine compound of Specific example (2)-4.

Identification of the guanidine compound of Specific Example (2)-4 was conducted using $^1$H-NMR (solvent: DMSO-$d_6$, 300 MHz). Data are shown below.

$^1$H-NMR (δ, ppm): 0.98 to 1.30 (m, 20 H), 1.56 (m, 4 H), 1.63 (m, 8 H), 1.86 (m, 8 H), 3.39 (m, 4 H), 4.74 (m, 4 H), 6.05 (d, 1 H), 6.16 (dd, 1 H), 7.06 (d, 1 H)

Synthesis of Guanidine Compound of Specific Example (3)-1

A mixture of 119 g of phenyl isocyanate and 1 g of 3-methyl-1-phenylphosphorene-1-oxide was heated and stirred under nitrogen flow while maintaining the inner temperature was kept at 50° C.

After completion of the gas generation, the mixture was cooled to room temperature and 0.8 liters of acetonitrile was added. To this was added a solution of 13 g of ethylenediamine in 200 ml of acetonitrile dropwise while the inner temperature was kept at 10° C. or less under ice cooling. The mixture was stirred at room temperature for 1 hour, then, the reaction mixture was added to 10 liters of water and the mixture was stirred. The precipitated crystals were filtered and dried to obtain 101 g of crystals of the guanidine compound of Specific example (3)-1.

Identification of the guanidine compound of Specific Example (3)-1 was conducted using $^1$H-NMR (solvent: DMSO-$d_6$, 300 MHz). Data are shown below.

$^1$H-NMR (δ, ppm): 3.36 (m, 4 H), 6.00 (m, 2 H), 6.79 (m, 8 H), 6.98 (m, 4 H), 7.10 (m, 8 H), 7.62 (m, 2 H)

Synthesis of Guanidine Compound of Specific Example (3)-2

105 g of crystals of the guanidine compound of Specific Example (3)-2 was obtained in the same manner as in Example 5 except that the 13 g of ethylenediamine was substituted by 15.7 g of 1,3-propaneiamine.

Identification of the guanidine compound of Specific Example (3)-2 was conducted using $^1$H-NMR (solvent: DMSO-$d_6$, 300 MHz). Data are shown below.

$^1$H-NMR (δ, ppm): 1.72 (t, 2 H), 3.21 (m, 4 H), 5.78 (m, 2 H), 6.81 (m, 8 H), 6.92 to 7.19 (m, 12 H), 7.58 (m, 2 H)

Next, the heat sensitive recording material of the present invention will be described specifically using examples.

EXAMPLE 1

[Preparation of Microcapsule Solution A]

To 19 parts of ethyl acetate was added 2.8 g of a diazonium salt (Exemplary compound (7)-2, maximum absorption wavelength: 370 nm) and 10 g of tricresyl phosphate and mixed uniformly. Then, to this mixture was added 7.6 g of Takenate D-110N (manufactured by Takeda Chemical Industries Ltd.) as a wall agent and mixed uniformly to obtain solution I.

Then, to this solution I was added 46 parts of an 8% by weight aqueous phthalated gelatin solution, 17.5 parts of water and 2 parts of a 10% aqueous sodium dodecylbenzenesulfonate solution, and the mixture was emulsified and dispersed for 10 minutes at 40° C. and 10000 r.p.m. To the resulting emulsion was added 20 parts of water and the mixture was made uniform. A microcapsulation reaction was then conducted for 3 hours at 40° C. while the mixture was stirred to obtain microcapsule liquid A. The average particle size of the microcapsules was from 0.7 to 0.8 μm.

[Preparation of Coupler Emulsion B]

To 10.5 parts of ethyl acetate was added 3.0 g of a coupler (Exemplary compound (10)), 3.0 parts of a guanidine compound of Specific Example (1)-3 as a base, 0.5 parts of tricresyl phosphate, and 0.24 parts of diethyl maleate to obtain solution II.

Then, 49 parts of a 15% by weight aqueous lime-treated gelatin solution, 9.5 parts of a 10% aqueous sodium dodecylbenzenesulfonate solution and 35 parts of water were mixed uniformly at 40° C., and to this was added the solution II and the mixture was emulsified and dispersed for 10 minutes at 40° C. and 10000 r.p.m. The resulting emulsion was stirred for 2 hours at 40° C. to removed ethyl acetate, then, the weight of vaporized ethyl acetate and water was compensated by water added to obtain a coupler emulsion B developing cyan color.

[Preparation of Heat Sensitive Recording Layer Coating Solution C]

3.6 parts of the microcapsule solution A, 3.3 parts of water and 9.5 arts of the coupler emulsion B were mixed uniformly to obtain heat sensitive recording layer coating solution C.

[Preparation of Protective Layer Coating Solution D]

100 parts of a 6% aqueous solution of itaconic acid-modified polyvinyl alcohol (trade name: KL-318, manufactured by Kuraray Co. Ltd.) and 10 parts of a 30% dispersion of epoxy-modified polyamide (trade name: FL-71, manufactured by Toho Chemical Industries Co. Ltd.) were mixed, and this mixed solution was mixed uniformly with 15 parts of a 40% zinc stearate dispersion (trade name: Hydrin Z, manufactured by Chukyo Yushi K. K.) to obtain protective layer coating solution D.

[Coating]

On a substrate for a developing paper prepared by laminating polyethylene onto high grade paper, the heat sensitive recording layer coating solution C and the protective layer coating solution D were respectively coated and dried at 50° C. sequentially in this order to obtain the intended heat sensitive recording material. The amounts coated in terms of solid were 8.0 g/m$^2$ and 1.2 g/m$^2$, respectively.

[Color Developing Test]

Thermal development was conducted using a thermal head (KST type) manufactured by Kyocera Corp. with the applied power and pulse width of the thermal head set so that the recording energy per unit area was 50 mJ/mm$^2$. The entire surface was irradiated for 15 seconds using an ultraviolet lamp having an emission center wavelength of 365 nm and a power of 40 W. The densities of image portions and background portions of the resulting sample were measured by a Macbeth densitometer.

EXAMPLE 2

A heat sensitive recording material was made and evaluated in the same manner as in Example 1 except that an emulsion was obtained using the guanidine compound of Specific Example (1)-1 as the base instead of the base used in Example 1.

EXAMPLE 3

A heat sensitive recording material was made and evaluated in the same manner as in Example 1 except that an emulsion was obtained using the guanidine compound of Specific Example (4)-5 as the base instead of the base used in Example 1.

EXAMPLE 4

A heat sensitive recording material was made and evaluated in the same manner as in Example 1 except that an emulsion was obtained using the guanidine compound of Specific Example (2)-4 as the base instead of the base used in Example 1.

EXAMPLE 5

A heat sensitive recording material was made and evaluated in the same manner as in Example 1 except that an emulsion was obtained using the guanidine compound of Specific Example (3)-1 as the base instead of the base used in Example 1.

EXAMPLE 6

A heat sensitive recording material was made and evaluated in the same manner as in Example 1 except that an emulsion was obtained using the guanidine compound of Specific Example (3)-2 as the base instead of the base used in Example 1.

EXAMPLE 7

A heat sensitive recording material was made and evaluated in the same manner as in Example 1 except that the coupler of Specific Example (62) was used instead of the coupler used in Example 1.

EXAMPLE 8

A heat sensitive recording material was made and evaluated in the same manner as in Example 1 except that the coupler of Specific Example (63) was used instead of the coupler used in Example 1.

Comparative Example 1

A heat sensitive recording material was made and evaluated in the same manner as in Example 1 except that an emulsion was obtained using triphenylguanidine as the base instead of the base used in Example 1.

Optical densities of image portions and non-image portions are shown in Table 3.

TABLE 3

|  | Optical density (Dc) on image portion | Optical density (Dc) on non-image portion |
|---|---|---|
| Example 1 | 1.82 | 0.09 |
| Example 2 | 1.78 | 0.09 |
| Example 3 | 1.77 | 0.10 |
| Example 4 | 1.80 | 0.09 |
| Example 5 | 1.75 | 0.10 |
| Example 6 | 1.77 | 0.10 |
| Example 7 | 1.75 | 0.07 |
| Example 8 | 1.81 | 0.07 |
| Comparative Example 1 | 1.41 | 0.10 |

EXAMPLE 9

An example of the production of a multi-layer heat sensitive recording material of the present invention is shown below which can conduct heat recording of three colors, yellow, magenta and cyan, independently and can reproduce a fullcolor image.

(1) Preparation of Diazo Compound—Comprising Capsule Solution (a) Preparation of Magenta Color Developing Maicrocapsule Solution (A)

4.4 parts of the following compound (A) having a maximum absorption wavelength of 420 nm as a diazonium compound was dissolved in 16.4 parts of ethyl acetate, and to this was further added 7.3 parts of isopropylbiphenyl and 2.5 parts of dibutyl phthalate, and mixed uniformly while being heated.

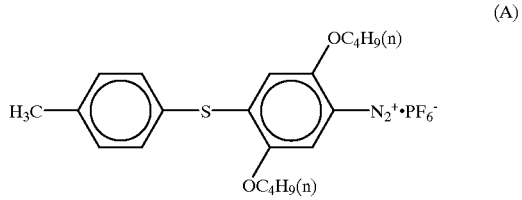

(A)

In the above-described mixture, 4.5 parts of the isocyanate compound (1) described in Synthesis Example 1 was added to 4.5 parts of a xylylene diisocyanate/trimethylolpropane adduct (Takenate D110N, 75% by weight ethyl acetate solution, manufactured by Takeda Chemical Industries, Ltd.) and 4.5 parts of a 30% by weight solution of a xylylene diisocyanate/bisphenol A adduct synthesized according to Japanese Patent Application No. 5-233536 in ethyl acetate as capsule wall materials, and the mixture was stirred uniformly.

Separately, 77 parts of a 6% by weight aqueous gelatin solution was prepared to which 0.96 parts of Scraph A G-8 (manufactured by Nippon Seika K. K.) had been added, to this was added the above-described mixture (solution) of the diazonium compound, and the mixture was emulsified and dispersed by a homogenizer. 20 parts of water was added to the resulting emulsion which was then made uniform. A capsulation reaction was then conducted for 3 hours while the mixture was stirred at 40° C. Next, the solution temperature was lowered to 35° C., 6.5 parts of an ion exchanged resin Amberlite IRA68 (manufactured by Organo Corp.) and 13 parts of Amberlite IRC50 (manufactured by Organo Corp.)were added, and the mixture was stirred for a further 1 hour. Subsequently, the ion exchanged resin was filtered, then, a 1% by weight aqueous hydroquinone solution was added in an amount of 0.4 parts per 10 parts of the capsule solution, and the mixture was stirred. Magenta developing microcapsule solution (A) of a diazonium compound was thus obtained. The average particle size of the capsules was 0.8 µm.

(b) Preparation of Cyan Developing Microcapsule Solution (B)

2.8 parts of a compound represented by the following formula (B-1) having a maximum absorption wavelength of 365 nm as a diazonium compound, 2.8 parts of dibutyl sulfate and 0.56 parts 2,2-dimethoxy-1,2-diphenylethane-1-one (Irgacure 651, manufactured by Ciba Geigy) were dissolved in 10.0 parts of ethyl acetate. Further, 5.9 parts of isopropylbiphenyl and 2.5 parts of tricresyl phosphate which are solvents having high boiling points were added, and mixed uniformly while being heated.

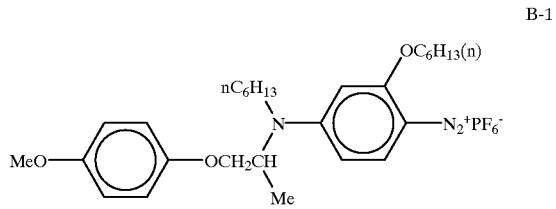

B-1

To the above-described mixed solution was further added 7.6 parts of xylylene diisocyanate/trimethylolpropane adduct (Takenate D110N; 75% by weight ethyl acetate solution, manufactured by Takeda Chemical Industries, Ltd.) as a capsule wall material, and the mixture was stirred uniformly. Separately, 64 parts of a 6% by weight aqueous gelatin (trade name: MGP-9066, manufactured by Nippi Gelatin Industry K. K.) solution was prepared to which 2.0 parts of a 10% by weight aqueous sodium dodecylsulfonate solution had been added. To this was added the above-described mixture of the diazonium compound, and the mixture was emulsified and dispersed by a homogenizer.

20 parts of water was added to the resulting emulsion which was then mad uniform and was reacted for 30 minutes at 40° C. while being stirred. Next, the mixture was heated to 60° C. and a capsulation reaction was conducted for 3 hours. Then, the solution temperature was lowered to 35° C., and to this was added 6.5 parts of an ion exchanged resin Amberlite IRA68 (manufactured by Organo Corp.), and 13 parts of Amberlite IRC50 (manufactured by Organo Corp.), and the mixture was stirred for a further 1 hour. Subsequently, the ion exchanged resin was filtered to obtain the intended cyan developing microcapsule solution (B). The average particle size of the capsules was 0.64 µm.

(c) Preparation of Yellow Developing Microcapsule Solution (C)

4.4 parts of a diazonium compound (C-1) and 7.5 parts of cumylbenzene were added to 17.5 parts of ethyl acetate and mixed uniformly. Then, to this mixed solution was added 4.4 parts of the following compound ((1)-4) and 3.3 parts of aliphatic isocyanate "Takenate D110N" (manufactured by Takeda Chemical Industries, Ltd.) as wall materials and the mixture further mixed to obtain solution (I). Then, the above-described solution (I) was added to a mixture of 60 parts of an 8% aqueous phthalated gelatin solution, 16.8 parts of water and 2 parts of a 10% aqueous sodium dodecylbenzenesulfonate solution, and the mixture was emulsified and dispersed for 10 minutes using a homogenizer at 40° C. and 5000 rpm. To the resulting emulsion was added 20 parts of water and 0.25 parts diethyltriamine and the mixture was made uniform. A capsulation reaction was then conducted for 1 hour at 40° C. while the mixture was being stirred, 30 parts of water were further added to the mixture and the capsulation reaction was conducted for a further 3 hours at 60° C. to obtain yellow developing microcapsule solution(C). The particle size of the capsules was 2.6 µm.

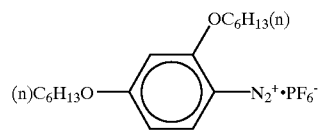

C-1

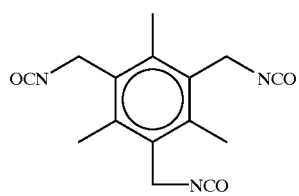

(1)-4

(2) Preparation of Coupler Emulsified Dispersion (d) Preparation of Magenta Color Developing Coupler Emulsion (D)

3.0 parts of the following coupler (D), 3.0 parts of triphenylguanidine, 0.5 parts of tricresyl phosphate and 0.24 parts of diethyl maleate were dissolved in 10.5 parts of ethyl acetate to obtain solution II.

Then, 49 parts of a 15% by weight aqueous lime-treated gelatin solution, 9.5 parts of a 10% aqueous sodium dodecylbenzenesulfonate solution and 35 parts of water were mixed uniformly and to this was added the solution II and the mixture was emulsified and dispersed for 10 minutes using a homogenizer at 40° C. and 10000 r.p.m. The resulting emulsion was stirred for 2 hours at 40° C. to remove the ethyl acetate, then the weight of the vaporized ethyl acetate and water was compensated for by water being added to obtain the magenta developing coupler emulsion (D).

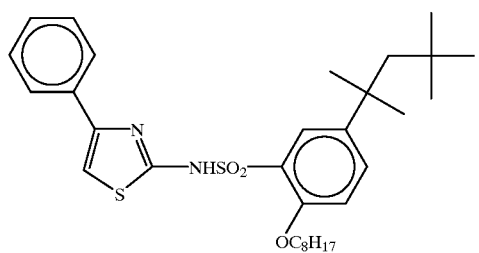

(D)

(e) Preparation of Cyan Developing Coupler Emulsion (E)

Cyan developing coupler emulsion (E) was obtained in the same manner as in Example 1.

(f) Preparation of Yellow Developing Coupler Emulsion (F)

Into 10 parts of ethyl acetate was dissolved 2 parts of 1-phenyl-3-(2,5-di-n-octyloxyphenyl)barbituric acid, 2 parts of 1,2,3-triphenylguanidine, 0.3 parts of tricresyl phosphate, and 0.1 parts of diethyl maleate. The resulting solution was added to an aqueous solution prepared by mixing 50 g of a 60% by weight aqueous gelatin solution and 2 g of a 2% by weight aqueous sodium dodecylbenzenesulfonate solution, then, the mixture was emulsified and dispersed for 10 minutes using a homogenizer to obtain a yellow developing coupler emulsion (F).

(3) Preparation of Coating Solution of Heat Sensitive Recording Layer

Capsule solution comprising a diazo compound and coupler emulsified dispersion were mixed according to the following combinations to obtain a coating solution. The ratio by weight of the capsule solution comprising a diazo compound to the coupler emulsified dispersion was 2:3.

| Coating solution | Diazo compound | Coupler |
|---|---|---|
| Magenta | (A) | (D) |
| Cyan | (B) | (E) |
| Yellow | (C) | (F) |

(4) Preparation of Coating Solution for Intermediate Layer

To 10 g of a 24% aqueous gelatin (trade name: #750, manufactured by Nitta Gelatin K. K.) solution was added 2.4 g of an acryl-styrene resin hollow capsule (trade name: Rohpake OP-62, manufactured by Rohm & Haas) and mixed uniformly to obtain intermediate layer solution.

(5) Preparation of Coating Solution for Protective Layer 100 g of a 6% aqueous itaconic acid-modified polyvinyl alcohol (trade name: KL-318, manufactured by Kuraray Co., Ltd.) solution and 10 g of a 30% epoxy-modified polyamide (trade name: FL-71, manufactured by Toho Chemical Industry Co., Ltd.) dispersion were mixed and to this mixture was added 15 g of a 40% zinc stearate (trade name: Hydrin Z. Manufactured by Chukyo Yushi K. K.) dispersion to obtain protective layer solution.

(Coating Solution for Back Layer)

1200 g of a 4% aqueous gelatin solution was used as the coating solution for the back layer.

(Preparation of Substrate Having Primer Layer Provided)

SBR latex was coated on both surfaces of a polyethylene terephthalate plate having a thickness of 175 μm at 0.3 g/m² in terms of solid weight, then, a coating solution for a primer layer described below was coated on both surface so that the solid weight per one surface was 0.1 g/m² to obtain a substrate provided with a primer layer.

(Preparation of Coating Solution for Primer Layer)

200 g of a 5% aqueous gelatin (#810, manufactured by Nitta Gelatin K. K.) solution, 0.5 g of gelatin dispersion in which a polymethyl methacrylate resin particle having a particle size of 2 μm had been dispersed in an amount of 5%, 1.0 g of a 3% aqueous 1,2-benzothiazoline-3-one solution, and 10 g of a 2% aqueous di(2-ethylhexyl) sulfonate solution were mixed to obtain the coating solution for the primer layer.

(6) Production of Multicolor Heat Sensitive Recording Material

The coating solution for a back layer was coated and dried so that the amount thereof was 1.8 g/M² in terms of solid weight (thickness after drying: 10 μm) on one surface of the transparent substrate provided with a primer layer.

Then, on the other surface, cyan heat sensitive color developing layer solution, intermediate layer solution, magenta heat sensitive color developing layer solution, intermediate layer solution, yellow heat sensitive color developing layer solution and protective layer solution were coated in this order from the substrate, on a slide using a slide type hopper-wise bead coating apparatus, and dried to obtain a multicolor heat sensitive recording material.

The amount coated of each solution was as follows: 6.1 g/m² for the cyan heat sensitive recording layer, 7.8 g/m² for the magenta heat sensitive recording layer, 2.4 g/m² for the intermediate layer (1.2 g/m² for gelatin, and 1.2 g/m² for the hollow capsule), 7.2 g/m² for the yellow heat sensitive recording layer, and 2.0 g/m² for the protective layer, in terms of solid weight after drying.

(7) Thermal Recording

Recording was conducted using the resulting recording materials.

A yellow image was recorded on the resulting recording material using a KST type thermal head (trade name, manufactured by Kyocera Corp.) while the recording heat energy per unit area was controlled via the applied voltage and pulse width so that the density at image portions measured by a Macbeth densitometer was 0.5.

Next, the recording material was exposed for 10 seconds to an ultraviolet lamp having a light emission center wavelength of 420 nm and a power of 40 W to conduct light fixation of the magenta heat sensitive color developing layer, then, a cyan image was recorded while the recording heat energy of the thermal head was controlled via the applied voltage and pulse width so that the density at image portions measured by a Macbeth densitometer was 0.5.

Next, the recording material was exposed for 30 seconds to an ultraviolet lamp having an emission center wavelength of 365 nm and a power of 40 W to conduct light fixation of the magenta heat sensitive color developing layer, then, a yellow image was recorded by while the recording heat energy of the thermal head was controlled via the applied voltage and pulse width so that the density at image portions measured by a Macbeth densitometer was 0.5.

As a result, image portions wherein yellow recording and magenta recording overlapped developed red color, image portions wherein magenta recording and cyan recording overlapped developed blue color, image portions wherein yellow recording and cyan recording overlapped developed green color, and image portions wherein yellow recording, magenta recording and cyan recording overlapped developed black color, in addition to each color developed image of yellow, magenta and cyan.

[Storability Test]

The heat sensitive recording material obtained according to the above-described method was stored for 3 days under conditions of a temperature of 40° C. and a humidity of 90%. Next, the heat sensitive recording material was exposed for 10 seconds to an ultraviolet lamp having a light emission center wavelength of 420 nm and a power of 40 W to conduct light fixation of the magenta color developing layer. Cyan developing was then conducted by controlling the applied voltage and pulse width so that the recording heat energy per unit area of the thermal head was 50 mJ/mm$^2$, and the densities of image portions and background portions were measured. The results are shown in Table 4. When the density does not vary before and after the storage test, the heat sensitive recording material is judged to have excellent storability.

EXAMPLE 10

A heat sensitive recording material was produced and evaluated in the same manner as in Example 9 except that the composition of the cyan developing coupler emulsified dispersion (E) in Example 9 was substituted by the composition in Example 2.

EXAMPLES 11 TO 16

Heat sensitive recording materials were produced and evaluated in the same manner as in Example 9 except that the composition of the cyan developing coupler emulsified dispersion (E) in Example 9 was substituted by the compositions in Examples 3 to 8.

Comparative Example 2

A heat sensitive recording material was produced and evaluated in the same manner as in Example 9 except that the composition of the cyan developing coupler emulsified dispersion (E) in Example 9 was substituted by the composition in Comparative Example 1.

Comparative Example 3

A heat sensitive recording material was produced and evaluated in the same manner as in Comparative Example 2 except that an emulsion was obtained using dicyclohexylphenylguanidine instead of triphenylguanidine as a base.

Optical densities of image portions and non-image portions before and after the storage test are shown in Table 4.

TABLE 4

| | Optical density (Dc) of image portion | | Optical density (Dc) of non-image portion | |
|---|---|---|---|---|
| | Before treatment | After treatment | Before treatment | After treatment |
| Example 9 | 1.21 | 1.19 | 0.10 | 0.11 |
| Example 10 | 1.18 | 1.16 | 0.10 | 0.11 |
| Example 11 | 1.17 | 1.14 | 0.11 | 0.12 |
| Example 12 | 1.20 | 1.18 | 0.10 | 0.10 |
| Example 13 | 1.17 | 1.14 | 0.10 | 0.11 |

TABLE 4-continued

| | Optical density (Dc) of image portion | | Optical density (Dc) of non-image portion | |
|---|---|---|---|---|
| | Before treatment | After treatment | Before treatment | After treatment |
| Example 14 | 1.18 | 1.17 | 0.11 | 0.13 |
| Example 15 | 1.19 | 1.15 | 0.09 | 0.10 |
| Example 16 | 1.20 | 1.15 | 0.09 | 0.10 |
| Comparative Example 2 | 0.89 | 0.65 | 0.12 | 0.15 |
| Comparative Example 3 | 1.15 | 0.72 | 0.11 | 0.13 |

From the results, it can be seen that the heat sensitive recording material using the guanidine compound of the present invention as a base has a higher color developing density as compared with the heat sensitive recording material using triphenylguanidine (irrespective of the type of couplers) as a base.

According to the present invention, there are provided a novel guanidine compound which is strongly basic and superior in diffusion resistance, and a novel diazo heat sensitive recording material which can develop color at a high image density by using a diazonium salt compound and a coupler as color developing components and by the inclusion of a guanidine compound as a base.

What is claimed is:

1. A heat sensitive recording material comprising a substrate supporting thereon a heat sensitive recording layer containing a diazonium salt compound, a coupler which reacts with the diazonium salt compound when heated to develop color, and a base, wherein the heat sensitive recording layer includes as the base at least one of the guanidine compounds represented by the general formula (2):

General formula (2)

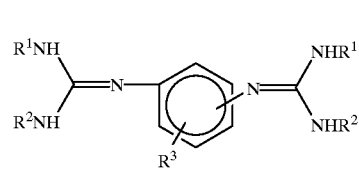

wherein in said general formula (2), $R^1$ and $R^2$ represent an alkyl group or aryl group and may be the same or different, and $R^3$ represents an alkyl group or halogen atom.

2. A heat sensitive recording material according to claim 1, wherein the heat sensitive recording material comprises as the coupler at least one of the pyrrolo (1,2-a)pyrimidine compounds represented by the following general formula (5):

General formula (5)

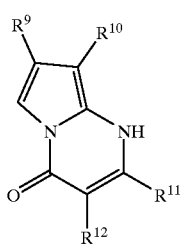

wherein, in the general formula (5), $R^9$ to $R^{12}$ represent a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group.

3. A heat sensitive recording material according to claim 1, wherein the maximum absorption wavelength $\lambda_{max}$ of said diazonium salt compound is 450 nm or less.

4. A heat sensitive recording material according to claim 1, wherein said diazonium salt compound is at least one selected from compounds represented by the following general formula (6), compounds represented by the following general formula (7) and compounds represented by the following general formula (8):

General formula (6)

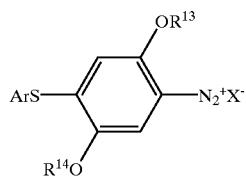

wherein, in said general formula (6), Ar represents a substituted or unsubstituted aryl group, each of $R^{13}$ to $R^{14}$ represents a substituted or unsubstituted alkyl group or a substituted or unsubstituted aryl group, and may be the same or different, and $X^-$ represents an acid anion;

General formula (7)

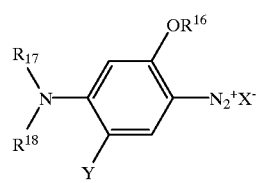

in said general formula (7), each of $R^{16}$, $R^{17}$ and $R^{18}$ represents a substituted or unsubstituted alkyl group or a substituted or unsubstituted aryl group and may be the same or different, Y represents a hydrogen atom or $-OR^{15}$ group, $R^{15}$ represents a substituted or unsubstituted alkyl group or a substituted or unsubstituted aryl group, and $X^-$ represents an acid anion;

General formula (8)

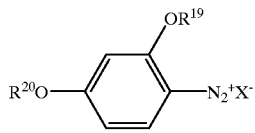

and said general formula (8), each of $R^{19}$ and $R^{20}$ represents a substituted or unsubstituted alkyl group or a substituted or unsubstituted aryl group, and $X^-$ represents an acid anion.

5. A heat sensitive recording material comprising a substrate supporting thereon a heat sensitive recording layer containing a diazonium salt compound, a coupler which reacts with the diazonium salt compound when heated to develop color, and a base, wherein the heat sensitive recording layer includes as the base at least one of the guanidine compounds represented by the general formula (2):

General formula (2)

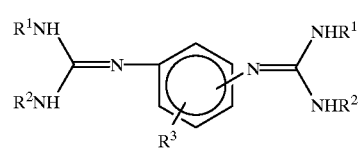

wherein in said general formula (2), $R^1$ and $R^2$ represent an alkyl group or aryl group and may be the same or different, and $R^3$ represents an alkyl group or halogen atom;

wherein the heat sensitive recording material comprises as the coupler at least one of the pyrrolo [1,2-a] pyrimidine compounds represented by the following general formula (5):

General formula (5)

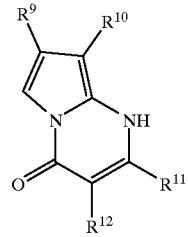

wherein, in the general formula (5), $R^9$ to $R^{12}$ represent a hydrogen atom, halogen atom, aryl group, alkyl group, cyano group, acyl group, substituted carbamoyl group, alkoxycarbonyl group, aryloxycarbonyl group, acyloxy group, alkoxy group, aryloxy group, alkylthio group, arylthio group, substituted sulfamoyl group, alkylsulfonyl group, arylsulfonyl group, alkylphosphoryl group, arylphosphoryl group or substituted amino group;

wherein said diazonium salt compound is at least one selected from compounds represented by the following general formula (6), compounds represented by the following general formula (7) and compounds represented by the following general formula (8):

General formula (6)

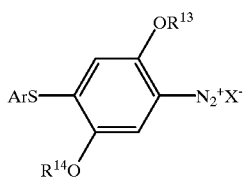

wherein, in said general formula (6), Ar represents a substituted or unsubstituted aryl group, each of $R^{13}$ to $R^{14}$ represents a substituted or unsubstituted alkyl group or a substituted or unsubstituted aryl group, and may be the same or different, and $X^-$ represents an acid anion, General formula (7)

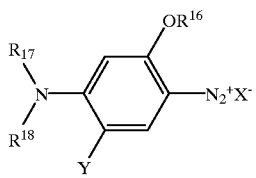

wherein, in said general formula (7), each of $R^{16}$, $R^{17}$ and $R^{18}$ represents a substituted or unsubstituted alkyl group or a substituted or unsubstituted aryl group and may be the same or different, Y represents a hydrogen atom or $-OR^{15}$ group, $R^{15}$ represents a substituted or unsubstituted alkyl group or a substituted or unsubstituted aryl group, and $X^-$ represents an acid anion, General formula (8)

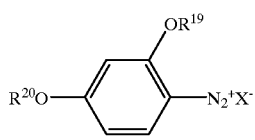

wherein, in said general formula (8), each of $R^{19}$ and $R^{20}$ represents a substituted or unsubstituted alkyl group or a substituted or unsubstituted aryl group, and $X^-$ represents an acid anion.

* * * * *